(12) United States Patent
Qi

(10) Patent No.: US 11,504,371 B2
(45) Date of Patent: Nov. 22, 2022

(54) QUINAZOLINES COMPOUND, PREPARATION METHOD THEREFOR AND APPLICATION THEREOF

(71) Applicant: Beijing Normal University, Beijing (CN)

(72) Inventor: Chuanmin Qi, Beijing (CN)

(73) Assignee: BEIJING NORMAL UNIVERSITY, Beijing (CN)

(*) Notice: Subject to any disclaimer, the term of this patent is extended or adjusted under 35 U.S.C. 154(b) by 108 days.

(21) Appl. No.: 16/816,922

(22) Filed: Mar. 12, 2020

(65) Prior Publication Data

US 2020/0206230 A1 Jul. 2, 2020

Related U.S. Application Data

(63) Continuation-in-part of application No. PCT/CN2017/116055, filed on Dec. 14, 2017.

(30) Foreign Application Priority Data

Sep. 13, 2017 (CN) .......................... 201710821016.2

(51) Int. Cl.
| | | |
|---|---|---|
| *A61K 31/519* | (2006.01) | |
| *A61K 9/00* | (2006.01) | |
| *A61K 31/337* | (2006.01) | |
| *A61K 31/44* | (2006.01) | |
| *A61K 35/00* | (2006.01) | |
| *C07D 491/056* | (2006.01) | |

(52) U.S. Cl.
CPC .......... *A61K 31/519* (2013.01); *A61K 9/0019* (2013.01); *A61K 9/0053* (2013.01); *A61K 31/337* (2013.01); *A61K 31/44* (2013.01); *A61K 35/00* (2013.01); *C07D 491/056* (2013.01)

(58) Field of Classification Search
CPC .... C07D 491/056; A61K 31/519; A61P 35/00
See application file for complete search history.

(56) References Cited

U.S. PATENT DOCUMENTS

2015/0018371 A1    1/2015 Cone et al.

FOREIGN PATENT DOCUMENTS

| CN | 101723846 A | 6/2010 |
| CN | 102026985 A | 4/2011 |
| CN | 103601730 A | 2/2014 |
| CN | 104230826 A | 12/2014 |
| CN | 105384745 A | 3/2016 |
| WO | WO2012127012 A1 | 9/2012 |

OTHER PUBLICATIONS

Kumar. Journal of Clinical Oncology, 2008, 10(1), 1742-1751. (Year: 2008).*
Xu. Bioorganic and Medicinal Chemistry, 2019, 27, 1-8, supporting information pp. 1-30. (Year: 2019).*

* cited by examiner

*Primary Examiner* — Noble E Jarrell
(74) *Attorney, Agent, or Firm* — Blank Rome LLP

(57) ABSTRACT

The present invention discloses a compound of anilino polyethylene glycol ether cycloquinazoline substituted with a substituted arylmethyl heteroatomic group having the structure of formula (I) below, or a pharmaceutically acceptable salt, ester or solvate thereof, and a pharmaceutical composition comprising the same. The compound and pharmaceutical composition disclosed herein can be used in tumor targeted therapy and in the regulation of tumors and related diseases.

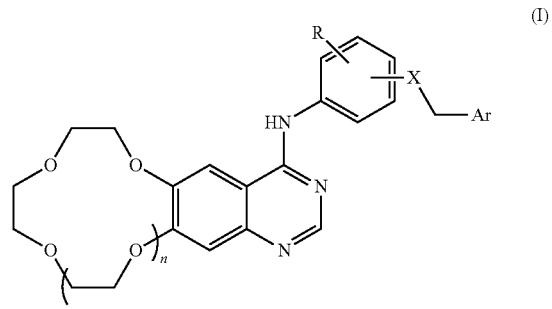

16 Claims, 5 Drawing Sheets

US 11,504,371 B2

QUINAZOLINES COMPOUND, PREPARATION METHOD THEREFOR AND APPLICATION THEREOF

CROSS-REFERENCE TO RELATED APPLICATIONS

This application is a continuation-in-part of International Application No. PCT/CN2017/116055, filed on Dec. 14, 2017, and claims priority of Chinese Patent Application No. 201710821016.2, filed on Sep. 13, 2017, the contents of both are incorporated herein by reference in its entirety.

FIELD OF THE INVENTION

The invention belongs to an integrated technical field of organic chemistry and medicinal chemistry. The invention relates to a new type of small molecule EGFR-TK (epidermal growth factor receptor tyrosine kinase) inhibitor having antitumor activity, and specifically relates to an anilino polyethylene glycol ether cycloquinazoline substituted at 4-position with a substituted arylmethylheteroatomic group or pharmaceutically acceptable salts thereof; pharmaceutical compositions and solvates containing the same; preparation method thereof; and use thereof for preparing molecular targeted antitumor therapeutic agent.

BACKGROUND OF THE INVENTION

Cancer is one of the diseases threatening human health at present. Cancer cells are characterized by unlimited proliferation causing high consumption of body's nutrients and the releasing of various toxins causing a series of symptoms in the body. Surgical treatment, radiotherapy and chemotherapy, as three main and traditional cancer therapies, can achieve certain anticancer effects with different mechanisms, but each has its limitations. Chemical drugs have special advantages in the treatment of tumors. They are the best in controlling the occult metastatic tumor focus in surgical or radiotherapy and the distant metastatic tumor all over the body. However, their main drawback is poorly selective inhibition of tumor cells and high toxicity.

With the development of molecular biology and the gradual understanding of the mechanism of tumor development, molecular targeted therapy of tumor has been developed rapidly. Targeted therapy is a new biological therapy mode, which can inhibit cell growth or promote apoptosis by blocking signal pathway directly or indirectly to achieve therapeutic effect. Targeted therapy, named as "biological missiles", targets at specific targets such as receptors, kinases, or molecular structures which are characteristics of tumor cells, leading to relatively slight side effects. A therapeutic drug is designed for definite carcinogenic sites, such that the therapeutic drug specifically binds to the carcinogenic sites once entering into the body, causing specific apoptosis of the tumor cell without affecting normal tissue around the tumor. Molecular targeted therapeutics of tumor include tyrosine kinase (TKs) inhibitors, monoclonal antibodies, anti-tumor angiogenesis therapeutics, Farnesyl protein transferase inhibitors, cyclin-dependent kinase inhibitors, and the like.

Cell transformation, proliferation and resistance to apoptosis occur mostly due to the overexpression or activation of TKs receptors leading to activation of downstream signaling pathways, which in turn triggers tumors. Therefore, blocking the signal transduction pathways of TKs receptor may prevent excessive proliferation of cells. More than 50% of proto-oncogene and oncogene products have tyrosine kinase activity, and their abnormal expression can directly lead to tumorigenesis. In addition, the kinase is also associated with tumor metastasis, angiogenesis and resistance to tumor chemotherapy. The research of small molecule inhibitors of tyrosine kinase has drawn attention in the research and development of anti-tumor drugs currently.

The quinazoline is a benzoheterocyclic compound with a formula of $C_8H_6N_2$, which is formed by fusing a benzene ring with a pyrimidine ring. Quinazoline and its derivatives have a wide range of medical and agricultural biological activities, and can be used as anti-inflammatory agents, antimicrobial agents, anti-malarial agents, antihypertensive drugs, anticonvulsants, anti-diabetes, cholinesterase inhibitors, sleep aids, DYRK1A inhibitors, antioxidants, dopamine D3 receptor inhibitors, antitumor agents, insect repellents, herbicides, etc. Especially in the field of anti-tumor drug research, a number of representative targeted medicines have been screened, such as Gefitinib, Erlotinib, Lapatinib, Icotinib, Vandetanib, etc., making the parent ring of quinazoline a focus for cancer drug research. The parent ring itself of quinazoline has tyrosine kinase inhibitory activity. The antitumor activity and selectivity of such compounds can be altered by changes in substituents at different positions on the quinazoline ring.

SUMMARY OF THE INVENTION

The inventor of the present invention synthesizes a series of novel compound of anilino polyethylene glycol ether cycloquinazoline substituted with a substituted arylmethyl heteroatomic group by changing the substituents on a phenylamino group, which is a substituent on 4-position of the quinazoline parent ring, with a substituted arylmethyl heteroatomic group. The antitumor activity of the compound is studied in vitro and in vivo. Surprisingly, this novel compound of anilino polyethylene glycol ether cycloquinazoline substituted with a substituted arylmethyl heteroatomic group can be used as a small molecule EGFR-TK inhibitor with medicinal values of high selectivity, high biological activity, low toxicity and high comprehensive therapeutic index, and can be used for preparation and clinical research applications of molecular targeted antitumor therapeutic drugs. The present invention has been achieved on this basis.

The purpose of the invention is to provide a novel compound of anilino polyethylene glycol ether cycloquinazoline substituted with a substituted arylmethyl heteroatomic group represented by formula (I), or a pharmaceutically acceptable salt, ester or solvate thereof, and a process for preparing the same. The present invention also provides a pharmaceutical composition comprising the above compound of formula (I) or a pharmaceutically acceptable salt, ester or solvate thereof. The present invention also provides use of the compound of formula (I) or the pharmaceutically acceptable salt, ester or solvate thereof, or a pharmaceutical composition comprising the same in the manufacture of a molecular targeted antitumor therapeutic agent, in particular in the manufacture of the therapeutic agent for treating prostate cancer, lung cancer, liver cancer, bowel cancer, stomach cancer, or pancreatic cancer, etc.

The purpose of the invention is achieved by the technical solution as follows.

The present invention firstly provides a compound of anilino polyethylene glycol ether cycloquinazoline substituted with a substituted arylmethyl heteroatomic group, having the structure of the following formula (I), or a pharmaceutically acceptable salt, ester or solvate thereof;

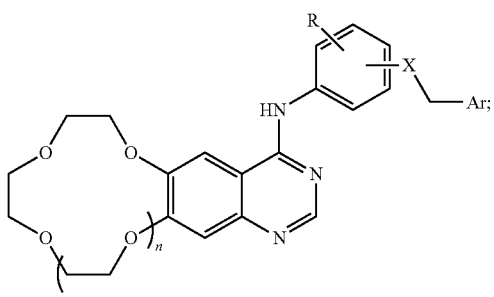

(I)

wherein, n is 0, 1, 2, 3, 4, 5 or 6; X represents —O—, —S—, —NH—, —SO—, —SO$_2$— or —CO—; R represents H—, F—, Cl—, Br—, I—, —CN, —CH$_3$, —CF$_3$ or —CCl$_3$; Ar represents monosubstituted, disubstituted, unsubstituted benzene, naphthalene, pyridine, furan, thiophene, indole, pyrimidine, benzopyrimidine, imidazole, thiazole, oxazole, benzoxazole or benzothiazole; when Ar is monosubstituted, the monosubstituent R$_1$ on Ar ring represents —NO$_2$, —CF$_3$, —C$_{13}$, —CBr$_3$, —CH$_2$CF$_3$, —H, F—, Cl—, Br—, —CH$_3$, —CH$_2$CHCH$_2$, —CN, —CHO, —COOH, —COOCH$_3$, —COOCH$_2$CH$_3$, —CONH$_2$, —CON(CH$_3$)$_2$, —N(CH$_3$)$_2$, —N(CH$_2$CH$_3$)$_2$, —OCH$_3$ or —OCH$_2$CH$_3$; when Ar is disubstituted, the disubstituents of R$_2$ and R$_3$ on the Ar ring independently represent F—, Cl—, Br—, —CH$_3$, CH$_3$O—, —CF$_3$, —CN, —CHO, —COOH, —COOCH$_3$, —COOCH$_2$CH$_3$, —CONH$_2$, —CON(CH$_3$)$_2$, —OCH$_3$, —N(CH$_3$)$_2$ or —N(CH$_2$CH$_3$)$_2$.

In a specific embodiment of the present invention, preferably, Ar in the present invention may be a substituted aromatic ring, which is 2-, 3- and 4-positions substituted arylmethyl heteroatomic group on an anilino group, respectively. Ar is as follows:

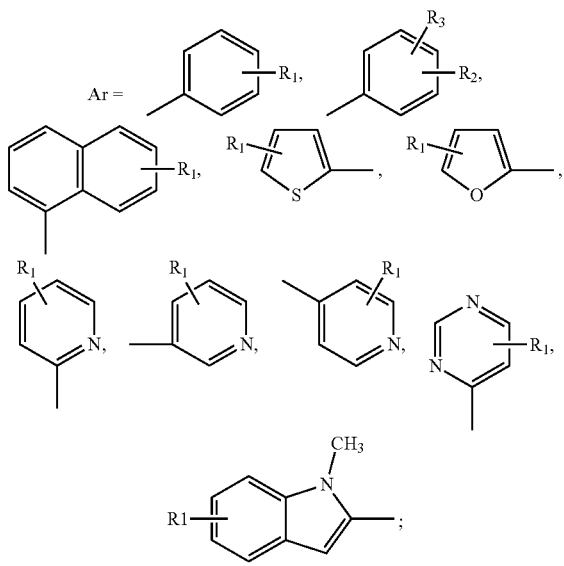

wherein R$_1$ may represent —NO$_2$, —CF$_3$, —CCl$_3$, —CBr$_3$, —CH$_2$CF$_3$, H—, F—, Cl—, Br—, —CH$_3$, —CH$_2$CHCH$_2$, —CN, —CHO, —COOH, —COOCH$_3$, —COOCH$_2$CH$_3$, —CONH$_2$, —N(CH$_3$)$_2$, —N(CH$_2$CH$_3$)$_2$, —OCH$_3$ or —OCH$_2$CH$_3$; R$_2$ and R$_3$ independently represent F—, Cl—, Br—, —CH$_3$, CH$_3$O—, —CF$_3$, —CN, —CHO, —COOH, —COOCH$_3$, —CONH$_2$, —OCH$_3$, —N(CH$_3$)$_2$ or —N(CH$_2$CH$_3$)$_2$.

In another embodiment of the present invention, n is 0, 1, 2 or 3, X represents —O—, —S— or —NH—; R represents H—, F—, Cl— or —CF$_3$; and Ar is

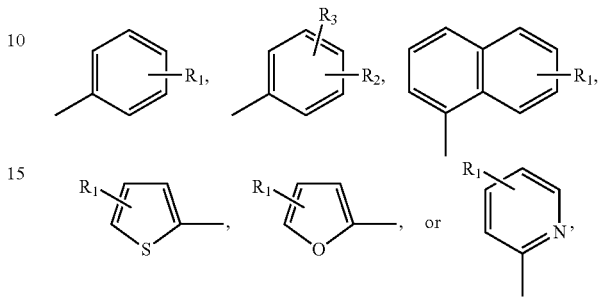

wherein R$_1$ represents —NO$_2$, —CF$_3$, —CCl$_3$, H—, Cl—, F—, —CH$_3$, —CN, —CHO, —COOH, —COOCH$_3$, —N(CH$_3$)$_2$ or —OCH$_3$; R$_2$ and R$_3$ independently represent —F, —Cl, —CH$_3$, CH$_3$O—, —CF$_3$, —CN, —CHO, —COOH or —N(CH$_3$)$_2$.

In a specific embodiment of the present invention, the compound of formula (I) of the present invention may optionally form a pharmaceutically acceptable salt with a pharmaceutically acceptable acid or base, including: (1) a salt formed with an inorganic acid or inorganic base, preferably hydrochloride, sulfate, phosphate and the like; (2) a salt formed with an organic acid or organic base, preferably citrate, p-toluenesulfonate, stearate, succinate, lactate, maleate, tartrate, palmitate, salicylate, dimethylamine salt, piperidine salt, morpholine salt and the like; (3) a pharmaceutically acceptable cation, preferably potassium, sodium, calcium, magnesium, aluminum, lithium, zinc and ammonium ions.

The present invention also provides a pharmaceutical composition comprising the compound of formula (I) or a pharmaceutically acceptable salt, ester or solvate thereof.

In a specific embodiment of the pharmaceutical composition provided by the present invention, the pharmaceutical composition further comprises a pharmaceutically acceptable carrier or excipient. Preferably, the pharmaceutically acceptable carrier or excipient comprises, but is not limited to, fillers, disintegrants, lubricants, glidants, effervescent agents, flavoring agents, preservatives, and coating materials.

Preferably, the carrier or excipient is selected from the group consisting of water, gelatin, lactose, starch, magnesium stearate, talc, vegetable oil, gum, alcohol, petrolatum, or combinations thereof.

In a specific embodiment of the pharmaceutical composition provided by the present invention, the pharmaceutical composition comprises a therapeutically effective amount of the above compound of formula (I) or a pharmaceutically acceptable salt, ester or solvate thereof. Preferably, the pharmaceutical composition can be formulated as a solid or liquid oral preparation, or an injection.

The present invention also provides use of the compound of formula (I) above or the pharmaceutically acceptable salt, ester, or solvate (for example, hydrate) thereof, or the pharmaceutical composition above, in the manufacture of an antitumor therapeutic drug, in particular in the manufacture of a molecular targeted antitumor therapeutic drug, more particularly in the manufacture of a therapeutic drug for treating cancers such as prostate cancer, lung cancer, liver cancer, colon cancer, stomach cancer, pancreatic cancer, neuroblastoma, breast cancer and the like.

In a specific embodiment of the use provided by the present invention, the drug further comprises a second therapeutic agent having an antitumor effect. Preferably, the second therapeutic agent is selected from, but not limited to, the group consisting of at least one of paclitaxel and docetaxel.

In a specific embodiment of the use provided by the present invention, the drug is used to treat or regulate tumors, preferably, to treat lung cancer, prostate cancer, liver cancer, intestinal cancer, stomach cancer, pancreatic cancer, neuroblastoma, breast cancer, head cancer, neck cancer, bone cancer, esophageal cancer, colon cancer, metastatic cancer, gynecologic or thyroid cancer, tumor angiogenesis and their complications.

The present invention also provides use of the above compound of formula (I), or the pharmaceutically acceptable salt, ester, solvate (e.g., hydrate) thereof, or a pharmaceutical composition as described above for treating disease.

The present invention also provides use of the above compound of formula (I), or the pharmaceutically acceptable salt, ester, solvate (e.g., hydrate) thereof, or a pharmaceutical composition as described above for treating or regulating tumor, preferably lung cancer, prostate cancer, liver cancer, intestinal cancer, stomach cancer, pancreatic cancer, neuroblastoma, breast cancer, head cancer, neck cancer, bone cancer, esophageal cancer, colon cancer, metastatic cancer, gynecologic or thyroid cancer, tumor angiogenesis and their complications.

In a specific embodiment of the present invention, the above compound of formula (I), or the pharmaceutically acceptable salt, ester, solvate (e.g., hydrate) thereof, or a pharmaceutical composition as described above of the present invention is used in combination with a second therapeutic agent having an antitumor effect for treating or regulating a tumor. The second therapeutic agent having an antitumor effect is selected from, but not limited to, the group consisting of at least one of paclitaxel and docetaxel.

The invention also provides a method of treating a disease, comprising administering to a patient in need thereof a therapeutically effective amount of the above compound of formula (I), or the pharmaceutically acceptable salt, ester, or solvate (e.g., hydrate) thereof, or a pharmaceutical composition as described above, wherein the disease comprises a tumor, preferably lung cancer, prostate cancer, liver cancer, intestinal cancer, stomach cancer, pancreatic cancer, neuroblastoma, breast cancer, head cancer, neck cancer, bone cancer, esophageal cancer, colon cancer, metastatic cancer, gynecologic or thyroid cancer, tumor angiogenesis and their complications.

The invention also provides a method of treating a disease, comprising administering to a patient in need thereof a therapeutically effective amount of a first therapeutic agent and a second therapeutic agent having an antitumor effect, the first therapeutic agent being selected from the above compound of formula (I), or the pharmaceutically acceptable salt, ester, solvate (e.g., hydrate) thereof, or a pharmaceutical composition as described above; the disease comprises a tumor, preferably lung cancer, prostate cancer, liver cancer, intestinal cancer, stomach cancer, pancreatic cancer, neuroblastoma, breast cancer, head cancer, neck cancer, bone cancer, esophageal cancer, colon cancer, metastatic cancer, gynecologic or thyroid cancer, tumor angiogenesis and their complications. The second therapeutic agent having antitumor effect is at least one selected from, but not limited to, the group consisting of paclitaxel and docetaxel.

The "therapeutically effective amount" used herein refers to an amount of the compound or pharmaceutical composition above, which is at least capable of alleviating the symptoms of a patient's condition when administered to a patient. The actual amount comprising a "therapeutically effective amount" will vary depending on a variety of circumstances including, but not limited to, particular condition being treated, severity of the condition, physique and health of the patient, and route of administration. Skilled medical practitioners can readily determine the appropriate amount using methods known in the medical arts.

The present invention further provides a method for preparing the above compound of formula (I) and the pharmaceutically acceptable salt thereof, comprising the following steps.

Synthesis of the Compound of Formula (I)

The anilino polyethylene glycol ether cycloquinazolines substituted with an arylmethyl heteroatomic group (I) and the pharmaceutically acceptable salt thereof according to the present invention can be synthesized by the following reactions.

Synthetic route 1: reacting the compound shown in formula (II) with aniline substituted with XH [i.e., the compound represented by formula (III)] to obtain a compound of formula (IV), and reacting the compound of formula (IV) with Y—CH$_2$Ar in the organic solvent to obtain the compound of formula (I);

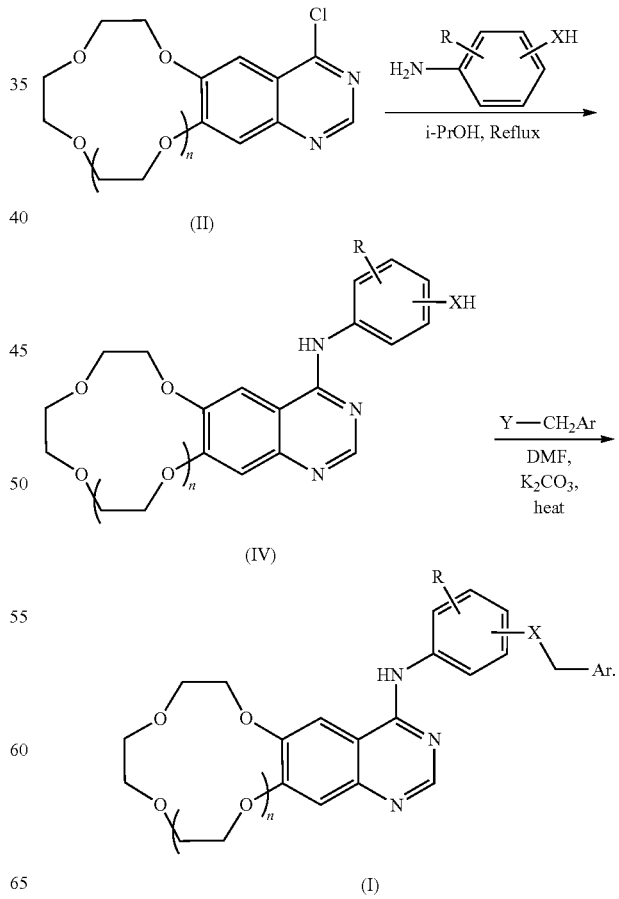

Synthetic route 2: reacting the compound of formula (III) with Y—CH$_2$Ar to obtain a compound of formula (V), and reacting the compound of formula (V) with the compound of formula (II), to obtain the compound of formula (I);

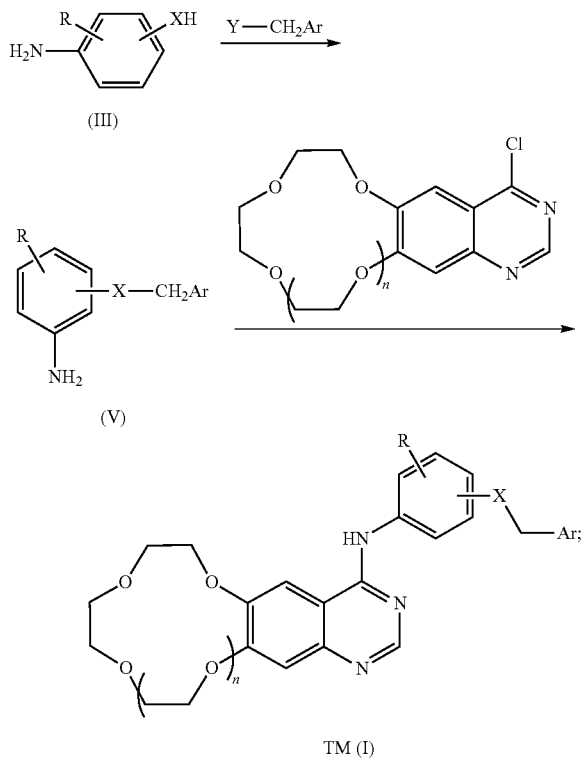

TM (I)

wherein Y in the above reaction reagent Y—CH$_2$Ar represents F, Cl, Br, I or a sulfonate group.

The starting materials necessary for the chemical synthesis of the anilino polyethylene glycol ether cycloquinazoline substituted with a substituted arylmethyl heteroatomic group represented by formula (I) or pharmaceutically acceptable salts thereof according to the present invention can be synthesized according to standard organic chemical procedures. The synthesis of these starting materials will be described in the following examples. Other necessary starting materials can be synthesized in accordance with similar procedures and methods as described in the Handbook of Organic Chemistry. The intermediate compound (IV) can be synthesized by reacting the compound (II) with an aminophenol (III) having hydroxyl or thiol at different positions on the benzene ring.

The intermediate compounds (IV) and (V) in the previous step of synthesizing the target compound (I) can be synthesized by reacting an aniline (III) substituted with different phenol or phenylthiol with the intermediate (II).

The biological activity of the compound of formula (I) are tested in the present invention, the details are as follows.

The antitumor activity are measured in vitro by MTT method in the present invention, and the test results show that the anilino polyethylene glycol ether cycloquinazoline substituted with a substituted arylmethyl heteroatomic group of formula (I) exhibit a good cell proliferation inhibitory activity against tumor cells such as HepG2, A549, DU145, MCF-7 and SH—SY5Y.

One of the anilino polyethylene glycol ether cycloquinazoline substituted with a substituted arylmethyl heteroatomic group of formula (I), N-(4-((4-nitrophenyl)methoxy)phenyl)-6,7-(benzo-9-crown-3)-4-quinazolinamine (i.e., compound 3 in Table 1), is studied by cell cycle experiments in the present invention. The results indicate that the target compound of the present invention mainly kill tumor cells in the G$_0$/G$_1$ phase. The percentage of cells in G$_0$/G$_1$ phase increases with the increase of drug concentration. That is, the target compound of formula (I) mainly act on the G$_0$ and G$_1$ phases of cancer cell growth, indicating that the target compound of the present invention is a targeted drug.

One of the anilino polyethylene glycol ether cycloquinazoline substituted with a substituted arylmethyl heteroatomic group of formula (I), N-(4-((4-nitrophenyl)methoxy)phenyl)-6,7-(benzo-9-crown-3)-4-quinazolinamine, is studied by cell membrane permeability test. Fluorescence observations of the effect of the target compound on the cell membrane indicate that the target compound can increase the permeability of the cell membrane, and Hoechst 33342 enters into the cells and binds to the DNA double strands. As the concentration of the target compound increases, the permeability is improved and the cells undergo apoptosis.

A part of the compound of anilino polyethylene glycol ether cycloquinazoline substituted with a substituted arylmethyl heteroatomic group represented by formula (I) are studied by detecting cell mitochondrial membrane potential and intracellular reactive oxygen species. The results show that the mitochondrial membrane potential of cancer cells (such as A549) is decreased and the cells undergo apoptosis after the treatment with the compound of formula (I). After the treatment of cells A549 with N-(4-((4-nitrophenyl)methoxy)phenyl)-6,7-(benzo-9-crown-3)-4-quinazolinamine, the increased intracellular reactive oxygen species (ROS) and apoptosis are measured by a fluorescence spectrometer.

In the present invention, the antitumor activity was evaluated by intraperitoneal injection to nude mice bearing different tumors, for compounds 3 (N-(4-((4-nitrophenyl)methoxy)phenyl)-6,7-(benzo-9-crown-3)-4-quinazolinamine) and 23 (compounds No. are shown in Table 1) (N-(3-((4-trifluoromethylphenyl)methoxy)phenyl)-6,7-(benzo-12-crown-4)-4-quinazolinamine) of formula (I).

Firstly, a tumor-bearing nude mouse model was established. 0.2-1 mL of cell suspension was inoculated subcutaneously into the left lower limb of nude mice, and the drug was administered when the tumor volume reached about 100 mm$^3$. Then, grouping and administration were performed; the nude mice (5 mice in each group) were randomly divided into several groups, such as ultra-pure water control group (blank), positive drug control group, and different dosage treatment groups. The nude mice in each group were administered continuously for 40 days. The nude mice were weighted every other day during the administration. Tumor volumes were measured and calculated. Then tumor growth curve, tumor inhibition curve (see FIGS. 1 and 3) and weight change curve (see FIGS. 2 and 4) were drawn. The results of antitumor activity in vivo of compound 23 show that compound 23 has a high inhibitory effect on nude mice bearing cancer cell DU145. Taxanes are identified as effective drugs for treating prostate cancer. Among those, docetaxel suffers from high cumulative neurotoxic toxicity and drug resistance although it has the best effect. Comparing to docetaxel, compound 23 has a much lower toxicity and drug resistance, and thus has a great development prospect. Compound 3 has a high inhibitory effect on nude mice bearing cancer cell A549, and its activity is similar to Iressa, a first-line therapeutic agent for treating lung cancer, and a slightly lower toxicity than that of Iressa.

In summary, the present invention provides a novel compound represented by formula (I), or pharmaceutically acceptable salts, esters and solvates thereof, and the pharmacodynamic tests thereof shows that some compounds of formula (I) have a cyclical blocking effect on cancer cells such as DU145 and A549, which are blocked in $G_0/G_1$ phase. After treatment with the compounds, the cell has increased cell membrane permeability, decreased mitochondrial membrane potential, and increased intracellular reactive oxygen species (ROS) level, inducing apoptosis in DU145, A549 and other cancer cells. These compounds have a high selectivity to different tumor cells and a high tumor inhibition activity. The treatment results of nude mice bearing DU145, A549 and other cancer cells shows that some target compounds have high activity, low toxicity and low drug resistance, and have a higher therapeutic index compared to traditional cancer chemotherapy methods. The chemotherapeutic drug of the invention has the advantages of high targeting and specificity, low toxicity and side effects, and the like. Some target compounds, such as compounds 3, 5, 13, 17, and 23, etc. (see Table 1 for compound numbers), can be used as molecular targeted chemotherapeutic drugs or lead compounds for treating malignant tumors with high selectivity. Some target compounds, such as compounds 29, 31, 34, and 35, etc. (numbers of these and the following compounds are shown in Table 1), can be used as broad-spectrum chemotherapeutic drugs or lead compounds for treating malignant tumors, and have broad clinical prospects.

DESCRIPTION OF THE DRAWINGS

In order to illustrate the technical solutions of the embodiments of the present invention and the prior art more clearly, the drawings used in the embodiments and the prior art are briefly introduced in the following. Obviously, the drawings described below represent only some embodiments of the present invention. Those skilled in the art can obtain other drawings according to the drawings without any creative work.

DETAILED DESCRIPTION OF THE INVENTION

Figure 1:
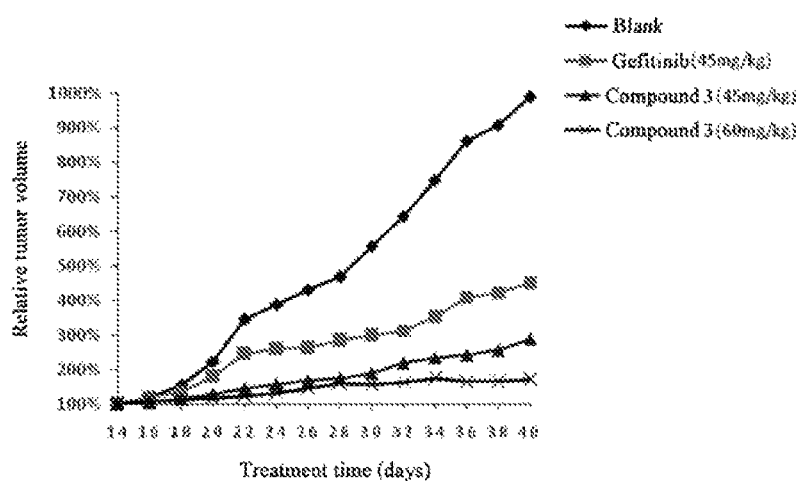
FIG. 1 shows the test results of inhibitory activity of compound 3 in examples of the present invention and a positive control drug in nude mice bearing tumor (A549) (a graph of the volumes of the treated tumor with respect to the number of experiment days).

The following are embodiments of the invention. The embodiments described are used to describe the present invention, such that it can be more clearly understood and implemented by those skilled in the art. The described embodiments are only a part of the embodiments of the invention rather than all of them. Based on the embodiments of the present invention, all other embodiments obtained by those skilled in the art without any creative work are within the scope of the present invention.

Example 1

Synthesis of N-(2-((4-nitrophenyl)methoxy) phenyl)-6,7-(benzo-9-crown-3)-4-quinazolinamine Structural formula of N-(2-((4-nitrophenyl)methoxy) phenyl)-6,7-(benzo-9-crown-3)-4-quinazolinamine is as follows:

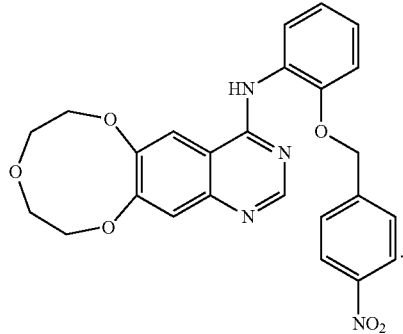 [SMILES: O=[N+]([O-])c1ccc(COc2ccccc2Nc2ncnc3cc4c(cc23)OCCOCCO4)cc1]

The intermediate compound (II) was firstly synthesized in steps 1.1 to 1.6. The last intermediate compound (IV) and the final product N-(2-((4-nitrophenyl) methoxy) phenyl)-6,7-(benzo-9-crown-3)-4-quinazolinamine were obtained in sequence.

1.1 Synthesis of diethylene glycol di-p-toluenesulfonate 10 mL (0.105 mol) of diethylene glycol, 300 mL of dichloromethane, and 40 g (0.21 mol) of p-toluenesulfonyl chloride were added in a 500 mL round bottom flask, and 47 g of potassium hydroxide (0.84 mol) was slowly added in the presence of an ice bath. The reaction was substantially completed over 1.5 h. The reaction liquid was washed with water (3×100 mL) for three times. The obtained organic phase was collected and dried with anhydrous $Na_2SO_4$. After filtration and evaporation of solvent, the crude product was obtained and recrystallized from ethanol to afford 40 g of white solid, in a yield 95%. The resulting spectra are consistent with those reported in literatures.

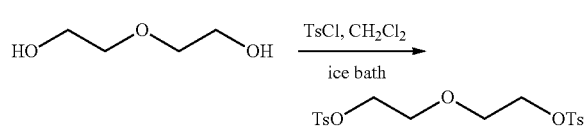

1.2 Synthesis of ethyl 3,4-(benzo-9-crown-3) Benzoate

In a 250 mL round bottom flask, 6.68 g (48.31 mmol) of potassium carbonate and 50 mL of DMF were added and heated to 120° C. for 30 min. 9.12 g (21.96 mmol) of diethylene glycol di-p-toluenesulfonate was dissolved in 60 mL of DMF, and 4 g (21.96 mmol) of ethyl 3,4-dihydroxybenzoate was dissolved in 30 mL of DMF. Both of the DMF solutions were mixed uniformly and then slowly added dropwise to the flask. The reaction was monitored by TLC, and completed over about 2 hours. The reaction liquid was cooled, filtered. The filtrate was evaporated to remove DMF. Then the reaction was added with 100 mL of dichloromethane, filtered, and the filtrate was dried by rotary evaporation to give brown oil, which was subjected to column chromatography (petroleum ether:ethyl acetate=6:1) to give 2.9 g of product as colorless oil, in a yield of 50%.

$^1$H NMR (400 MHz, CDCl$_3$): δ 7.63-7.59 (m, 2H, ArH), 6.90 (d, J=8.4 Hz, 1H, ArH), 4.50-4.48 (m, 2H, —OCH$_2$), 4.26 (q, J=7.2 Hz, 2H, —COOCH$_2$), 4.22-4.20 (m, 2H, —OCH$_2$), 3.87-3.81 (m, 4H, —OCH$_2$), 1.38 (t, J=7.2 Hz, 3H, —CH$_3$). $^{13}$C NMR (100 MHz, CDCl$_3$) δ 160.55, 157.20, 150.17, 145.17, 120.69, 120.03, 116.55, 68.70, 67.35, 67.22, 66.57, 55.49, 9.03 MS (ESI$^+$) m/z: 253.1 [M+H$^+$].

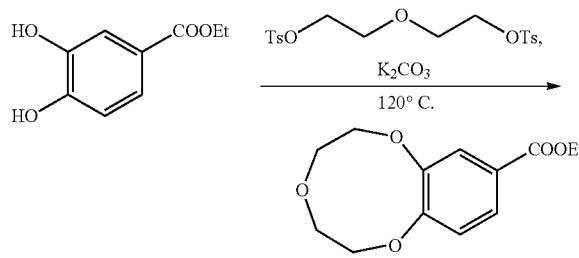

1.3 Synthesis of ethyl 6-nitro-3,4-(benzo-9-crown-3)benzoate

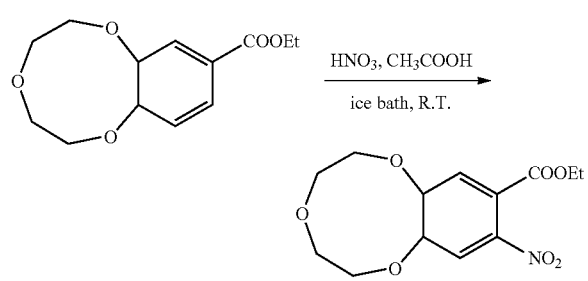

In the presence of an ice bath, 2.6 g (10.4 mmol) of ethyl 3,4-(benzo-9-crown-3) benzoate and 5 mL of glacial acetic acid were added into a round bottom flask. Under stirring, 6 mL (187.2 mmol) of concentrated nitric acid was slowly added dropwise. 30 min after the addition was completed, the system was warmed to room temperature and the reaction was performed for another 24 h. Then, the reaction liquid was poured into 200 mL of ice water, then extracted with dichloromethane (3×100 mL), washed with saturated sodium bicarbonate (2×100 mL) followed by water (2×100 mL) and saturated NaCl (2×100 mL), dried with anhydrous Na$_2$SO$_4$, filtered and rotary evaporated to dryness. 2 g of product was obtained as yellow oil, in a yield of 70%, which was directly used for the next reaction.

1.4 Synthesis of ethyl 6-amino-3,4-(benzo-9-crown-3)benzoate

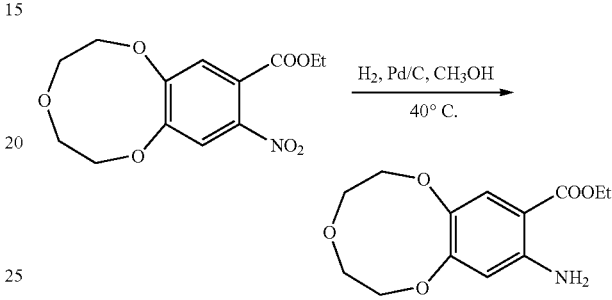

2 g (6.72 mmol) of ethyl 6-amino-3,4-(benzo-9-crown-3) benzoate was dissolved in 30 mL of methanol, and added with 0.6 g of palladium carbon (10%). Hydrogen gas was introduced. The reaction was completed after 13 h and filtrated over celite to remove the palladium carbon. The solvent was rotary evaporated to give 1.5 g of product as brown oil in a yield of 70%, which was put into the next reaction immediately.

1.5 Synthesis of 6,7-(benzo-9-crown-3)quinazolin-4-one

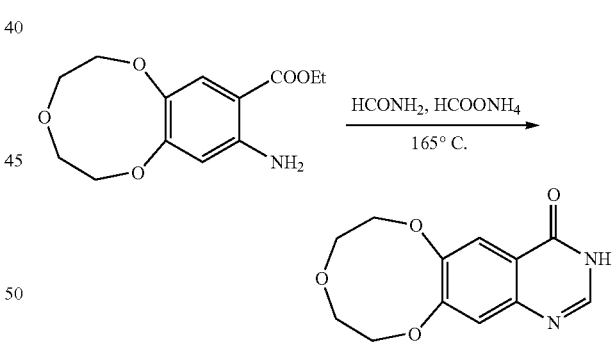

1.5 g (5.61 mmol) of ethyl 6-amino-3,4-(benzo-9-crown-3)benzoate was dissolved in 10 mL of formamide, and added with 0.975 g (15.09 mmol) of ammonium formate. The mixture was slowly heated to 165° C. to perform the reaction for 4 h. After the reaction was cooled to room temperature, solid was precipitated and filtrated to give 0.7 g of white powdery solid, in a yield of 50%.

$^1$H NMR (400 MHz, DMSO-d6). δ 12.06 (s, 1H, ArH), 7.96 (s, 1H, ArH), 7.64 (s, 1H, ArH) 7.18 (s, 1H, ArH), 4.57-4.55 (m, 2H, —OCH$_2$), 4.32-4.30 (m, 2H, —OCH$_2$), 3.84-3.83 (m, 4H, —OCH$_2$). $^{13}$C NMR (100 MHz, DMSO-d6) δ 162.82, 159.76, 157.12, 151.09, 145.91, 144.52, 118.63, 117.96, 74.75, 72.39, 71.80, 71.24. MS (ESI m/z: 249.2 [M+H$^+$].

1.6 Synthesis of 4-chloro-6,7-(benzo-9-crown-3)quinazoline

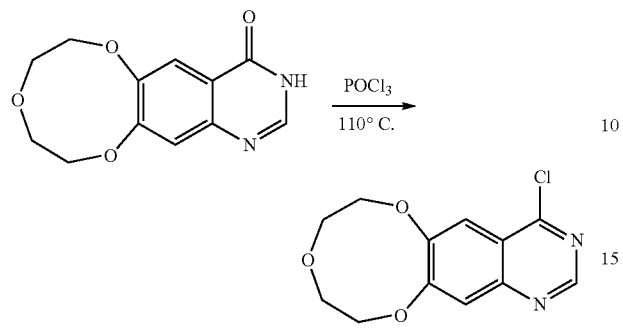

0.3 g (1.2 mmol) of 6,7-(benzo-9-crown-3) quinazolin-4-one and 1.5 mL (20.78 mmol) of phosphorus oxychloride were sequentially added to a single-neck flask under electromagnetic stirring, and heated to 110° C. to reflux for 4 h. After the completion of the reaction, phosphorus oxychloride was removed by rotary evaporation. 30 ml of saturated NaHCO$_3$ was added, and the mixture was extracted with dichloromethane (3×20 mL). The organic phase was combined, washed with water (2×20 mL) followed by saturated NaCl (2×20 mL) and dried over anhydrous Na$_2$SO$_4$. The solvent was rotary evaporated to give yellow oil. 0.21 g of a white solid was obtained by column chromatography (petroleum ether:ethyl acetate=3:1), in a yield of 65%.

$^1$H NMR (400 MHz, CDCl$_3$): δ 8.88 (s, 1H, ArH), 7.80 (s, 1H, ArH), 7.59 (s, 1H, ArH), 7.26 (s, 1H, ArH), 4.68-4.66 (m, 2H, —OCH$_2$), 4.51-4.49 (m, 2H, —OCH$_2$), 3.98-3.95 (m, 4H, —OCH$_2$). $^{13}$C NMR (100 MHz, DMSO-d6) δ 158.59, 1:57.44, 151.82, 146.56, 139.89, 119.64, 116.73, 114.38, 75.10, 71.90, 71.80, 70.83. MS (ESI$^+$) m/z: 267.1 [M+H$^+$].

1.7 Synthesis of N-(2-hydroxyphenyl)-6,7-(benzo-9-crown-3)-4-quinazolinamine

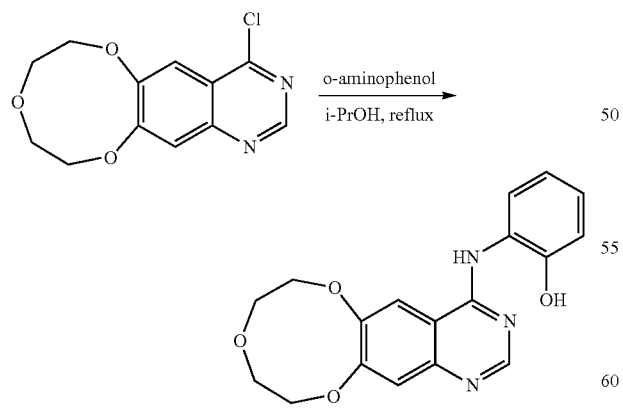

190 mg (0.7 mmol) of 4-chloro-6,7-(benzo-9-crown-3) quinazoline was dissolved in 12 mL of isopropanol, and added with 126 mg of o-aminophenol (1.15 mmol). The mixture was heated to reflux. After reacting for about 2 h, yellow solid appeared. The completion of the reaction was monitored by TLC. The reaction was placed stationarily to cool and suction filtered to give 168 mg of pale yellow solid (yield: 70.7%, m.p. 237° C.).

$^1$H NMR (400 MHz, DMSO-d$_6$): δ11.12 (s, 1H, —NH), 9.90 (s, 1H, —OH), 8.71 (s, 1H, ArH), 8.55 (s, 1H, ArH), 7.41 (s, 1H, ArH), 7.31 (d, J=7.8 Hz, 1H, ArH), 7.220, J=7.4 Hz, 1H, ArH), 7.03 (d, J=8.1 Hz, 114, ArH), 6.90 (t, J=7.8 Hz, 1M, ArH), 4.78 (brs, 2H, —CH$_2$), 4.43 (brs, 2H, —CH$_2$), 3.89 (brs, 4H, —CH$_2$).

1.8 Synthesis of N-(2-((4-nitrophenyl) methoxy) phenyl)-6,7-(benzo-9-crown-3)-4-quinazolinamine

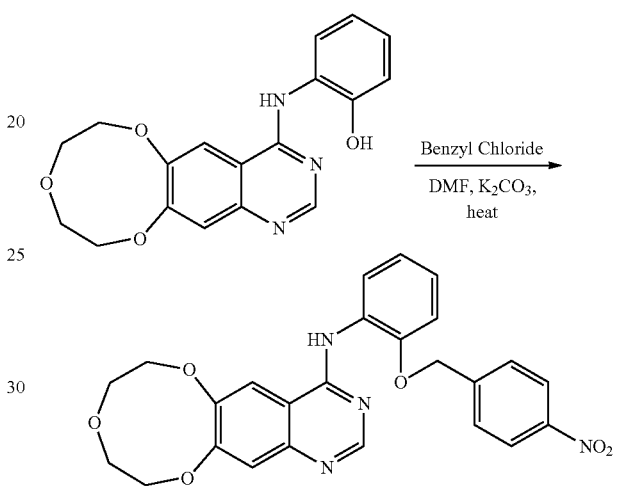

100 mg of N-(2-hydroxyphenyl)-6,7-(benzo-9-crown-3)-4-quinazolinamine (0.3 mmol), 250 mg (1.8 mmol) potassium carbonate, 16 mg (0.06 mmol) of 18-crown-6, 5 mg (0.03 mmol) KI was sequentially added to 2.5 mL of acetone, stirred at 35° C. for 0.5 h, then added with 45 μL of p-nitrobenzyl chloride (0.4 mmol), and stirred for another 6 h. The completion of the reaction was monitored by TLC. After the reaction was cooled to room temperature, it was poured into ice water and suction filtered to give bright yellow solid. The bright yellow solid was added to 5 mL of methanol, stirred for 0.5 h in the presence of an ice bath, and suction filtered, to give a pale yellow solid, in a yield of 40%, m.p. 192-193° C.

$^1$H NMR (400 MHz, DMSO-d6): δ 9.26 (s, 1H, —NH), 8.35 (s, 1H, ArH), 8.14 (s, 1H, ArH), 8.11 (d, J=5.2 Hz, 2H, ArH), 7.61 (d, J=8.5 Hz, 2H, ArH), 7.57 (d, J=7.8 Hz, 1H, ArH), 7.27 (s, 1H, ArH), 7.22 (t, J=7.3 Hz, 1H, ArH), 7.11 (d, J=8.0 Hz, 1H, ArH), 7.04 (1, J=7.5 Hz, 1H, ArH), 5.32 (s, 2H, —CH$_2$), 4.56 (brs, 2H, —CH$_2$), 4.39 (brs, 3.87 (brs, 4H, —CH$_2$). $^{13}$C NMR (100 MHz, DMSO-d6): δ157.78, 156.86, 154.06, 152.20, 151.46, 147.34, 146.77, 146.77, 145.17, 127.89, 127.56, 127.56, 126.48, 123.27, 123.27, 120.94, 117.75, 115.02, 113.39, 110.94, 74.88, 72.85, 71.86, 71.37, 68.45, MS (ESI$^+$) m/z: 475.2[M–H]$^+$ Example 2

Synthesis of N-(3-((p-nitrophenyl)methoxy)phenyl)-6,7-(benzo-9-crown-3)-4-quinazolinamine N-(3-hydroxyphenyl)-6,7-(benzo-9-crown-3)-4-quinazolinamine was firstly synthesized in steps 2.1-2.7. Steps 2.1-2.7 were similar as steps 1.1-1.7 in Example 1, except that o-aminophenol as starting material was replaced with 3-aminophenol.

2.8 Synthesis of N-(3-((p-nitrophenyl)methoxy)phenyl)-6,7-(benzo-9-crown-3)-4-quinazolinamine 100 mg (0.3 mmol) of N-(3-hydroxyphenyl)-6,7-(benzo-9-crown-3)-4-quinazolinamine, 250 mg (1.8 mmol) of potassium carbonate, 16 mg (0.06 mmol) of 18-crown-6, 5 mg (0.03 mmol) of KI was sequentially added to 2.5 mL of acetone, stirred at 35° C. for 0.5 h, then added with 45 μL (0.4 mmol) of p-nitrobenzyl chloride, and stirred for another 6 h. The completion of the reaction was monitored by TLC. After the reaction was cooled to room temperature, the reaction liquid was poured into ice water and suction filtered to give bright yellow solid. The bright yellow solid was added to 5 mL of methanol, stirred for 0.5 h in the presence of an ice bath, and suction filtered to give off-white solid, in a yield of 42%, m.p. 197-198° C.

$^1$H NMR (400 MHz, DMSO-d6): δ 9.48 (s, 1H, —NH), 8.48 (s, 1H, ArH), 8.29 (s, 1H, ArH), 8.27 (s, 1H, ArH), 8.24 (s, 1H, ArH), 7.76 (s, 1H, ArH), 7.74 (s, 2H, ArH), 7.47 (d, J=7.8 Hz, 1H, ArH), 7.29 (s, 1H, ArH), 6.78 (dd, J=8.0 Hz, 1H, ArH), 5.31 (s, 2H, —CH$_2$), 4.57 (s, 2H, —CH$_2$), 4.42 (s, 2H, —CH$_2$), 3.87 (s, 4H, —CH$_2$). $^{13}$C NMR (100 MHz, DMSO-d6): δ 157.96, 156.93, 156.52, 153.57, 151.50, 147.47, 146.94, 145.08, 140.70, 129.19, 128.12, 128.12, 123.53, 123.53, 117.82, 115.16, 114.56, 111.12, 109.37, 108.60, 74.92, 72.82, 71.78, 71.37, 68.05. MS (ESI+) m/z: 475.4[M−H]$^+$

Example 3

Synthesis of N-(4-((4-nitrophenyl)methoxy)phenyl)-6,7-(benzo-9-crown-3)-4-quinazolinamine N-(4-hydroxyphenyl)-6,7-(benzo-9-crown-3)-4-quinazolinamine was firstly synthesized in steps 3.1-3.7. Steps 3.1-3.7 were similar as steps 1.1-1.7 in Example 1, except that o-aminophenol was replaced with 4-aminophenol as starting material.

3.8 Synthesis of N-(4-((4-nitrophenyl)methoxy)phenyl)-6,7-(benzo-9-crown-3)-4-quinazolinamine The synthesis procedure was similar to that in Step 1.8 of Example 2 except that the reaction starting material N-(2-hydroxyphenyl)-6,7-(benzo-9-crown-3)-4-quinazolinamine was replaced with N-(4-hydroxyphenyl)-6,7-(benzo-9-crown-3)-4-quinazolinamine; the product was obtained as off-white solid, yield 36%, m.p. 192-193° C.

$^1$H NMR (400 MHz, DMSO-d6): δ 9.45 (s, 1H, —NH), 8.39 (s, 1H, ArH), 8.28 (d, J=8.6 Hz, 2H, ArH), 8.19 (s, 1H, ArH), 7.74 (d, J=8.6 Hz, 2H, ArH), 7.71 (d, J=8.9 Hz, 2H, ArH), 7.26 (s, 1H, ArH), 7.06 (d, J=8.9 Hz, 2H, ArH), 5.30 (s, 2H, —CH$_2$), 4.56 (brs, 2H, —CH$_2$), 4.40 (brs, 2H, —CH$_2$), 3.86 (brs, 4H, —CH$_2$). $^{13}$CNMR (100 MHz, DMSO-d6). δ 156.78, 156.71, 154.14, 153.82, 151.35, 147.35, 146.94, 145.18, 132.73, 128.15, 128.15, 123.88, 123.88, 123.54, 123.54, 117.75, 115.16, 114.67, 114.67, 110.96, 74.91, 72.82, 71.81, 71.39, 68.20. MS (ESI+) m/z: 475.1[M−H]$^+$

Example 4

Synthesis of N-(2-((4-fluorophenyl)methoxy)phenyl)-6,7-(benzo-9-crown-3)-4-quinazolinamine Steps 4.1-4.7 were completely consistent with steps 1.1-1.7 in Example 1. N-(2-hydroxyphenyl)-6,7-(benzo-9-crown-3)-4-quinazoline was firstly synthesized in steps 4.1-4.7.

4.8 Synthesis of N-(2-((4-fluorophenyl)methoxy)phenyl)-6,7-(benzo-9-crown-3)-4-quinazolinamine The synthesis procedure was similar to that in Step 1.8 in Example 1, except that p-nitrobenzyl chloride was replaced with 4-fluorobenzyl chloride as starting material; and white solid was obtained (yield: 41%, m.p. 140-141° C.).

$^1$H NMR (400 MHz, DMSO-d6): δ 9.19 (s, 1H, —NH), 8.33 (s, 1H, ArH), 8.10 (s, 1H, ArH), 8.06 (d, J=1.1 Hz, 2H, ArH), 7.60 (d, J=8.5 Hz, 2H, ArH), 7.51 (d, 1H, ArH), 7.30 (s, 1H, ArH), 7.24 (t, J=7.3 Hz, 1H, ArH), 7.20 (d, J=8.0 Hz, 1H, ArH), 7.06 (s, 1H, ArH), 7.03 (t, J=6.7 Hz, 1H, ArH), 5.18 (s, 2H, —CH$_2$), 4.57 (brs, 2H, —CH$_2$), 4.37 (brs, 2H, —CH$_2$), 3.89 (brs, 4H, —CH$_2$). $^{13}$CNMR (100 MHz, DMSO-d6): δ 157.69, 156.83, 154.05, 152.19, 151.44, 147.33, 146.55, 146.55, 144.39, 128.01, 127.54, 127.54, 126.51, 123.35, 123.28, 120.67, 117.74, 114.99, 113.38, 110.95, 74.90, 72.84, 71.87, 71.37, 68.57. MS (ESI+) m/z: 448.1[M−H]$^+$

Example 5

Synthesis of N-(3-((p-fluorophenyl)methoxy)phenyl)-6,7-(benzo-9-crown-3)-4-quinazolinamine N-(3-hydroxyphenyl)-6,7-(benzo-9-crown-3)-4-quinazolinamine was firstly synthesized in steps 5.1-5.7. Steps 5.1-5.7 were similar to steps 1.1-1.7 in Example 1, except that o-aminophenol was replaced with 3-aminophenol as starting material.

5.8 Synthesis of N-(3-((p-fluorophenyl)methoxy)phenyl)-6,7-(benzo-9-crown-3)-4-quinazolinamine The synthesis procedure was similar to that in step 1.8 of Example 1, except that p-nitrobenzyl chloride and N-(2-hydroxyphenyl)-6,7-(benzo-9-crown-3)-4-quinazolinamine were replaced with 4-fluorobenzyl chloride and N-(3-hydroxyphenyl)-6,7-(benzo-9-crown-3)-4-quinazolinamine, respectively, as starting materials. The product was obtained as pale yellow solid in a yield of 43%, m.p. 215-216° C.

$^1$H NMR (400 MHz, DMSO-d6): δ 9.47 (s, 1H, —NH), 8.48 (s, 1H, ArH), 8.28 (s, 1H, ArH), 8.25 (s, ArH), 8.22 (s, 1H, ArH), 7.74 (s, 1H, ArH), 7.69 (s, 2H, ArH), 7.42 (d, J=7.8 Hz, 1H, ArH), 7.23 (s, 1H, ArH), 7.10 (s, 1H, ArH), 6.77 (dd, J=8.0 Hz, 1H, ArH), 5.16 (s, 2H, —CH$_2$), 4.60 (brs, 2H, —CH$_2$), 4.48 (brs, 2H, —CH$_2$), 3.89 (brs, 4H, —CH$_2$). $^{13}$C NMR (100 MHz, DMSO-d6). δ 158.22, 156.57, 156.23, 153.45, 151.32, 147.31, 140.50, 137.00, 129.02, 128.18, 128.20, 127.72, 127.61, 127.61, 117.77, 115.03, 114.22, 111.10, 109.21, 108.44, 74.69, 72.45, 71.79, 71.36, 69.21. MS (ESI+) 448.1[M−H]$^+$

Example 6

Synthesis of N-(4-((4-fluorophenyl)methoxy)phenyl)-6,7-(benzo-9-crown-3)-4-quinazolinamineN-(4-hydroxyphenyl)-6,7-(benzo-9-crown-3)-4-quinazolinamine was firstly synthesized in steps 6.1-6.7. Steps 6.1-6.7 were similar as steps 1.1-1.7 in Example 1, except that o-aminophenol was replaced with 4-aminophenol as starting material.

6.8 The synthesis of N-(4-((4-fluorophenyl)methoxy)phenyl)-6,7-(benzo-9-crown-3)-4-quinazolinamine was similar to that of Step 1.8 in Example 1, except that p-nitrobenzyl chloride and N-(2-hydroxyphenyl)-6,7-(benzo-9-crown-3)-4-quinazolinamine were replaced with 4-fluorobenzyl chloride and N-(4-hydroxyphenyl)-6,7-(benzo-9-crown-3)-4-quinazolinamine, respectively, as starting material. The product was obtained as off-white solid in a yield of 40%, m.p. 222-223° C.

$^1$H NMR (400 MHz, DMSO-d6): δ 9.45 (s, 1H, —NH), 8.39 (s, 1H, ArH), 8.28 (d, J=8.6 Hz, 2H, ArH), 8.19 (s, 1H, ArH), 7.74 (d, J=8.6 Hz, 2H, ArH), 7.71 (d, J=8.9 Hz, 2H, ArH), 7.26 (s, 1H, ArH), 7.06 (d, J=8.9 Hz, 2H, ArH), 5.26 (s, 2H, —CH$_2$). 4.51 (brs, 2H, —CH$_2$), 4.33 (brs, 2H, —CH$_2$), 3.81 (brs, 4H, —CH$_2$). $^{13}$C NMR (100 MHz, DMSO-d6): δ 156.68, 156.66, 154.12, 153.81, 151.35, 147.33, 142.12, 133.04, 128.26, 128.12, 128.02, 125.36, 125.28, 125.21, 125.09, 123.69, 122.92, 118.01, 115.36, 114.62, 111.05, 75.12, 72.72, 71.83, 71.34, 68.53. MS (ESI+) m/z: 448.2 [M−H]$^+$ Example 7

Synthesis of N-(2-((4-trifluoromethylphenyl)methoxy) phenyl)-6,7-(benzo-9-crown-3)-4-quinazolinamine Steps 7.1-7.7 were completely consistent with steps 1.1-1.7 in Example 1. N-(2-hydroxyphenyl)-6,7-(benzo-9-crown-3)-4-quinazoline was firstly synthesized in steps 7.1-7.7.

7.8 Synthesis of N-(2-((4-trifluoromethylphenyl)methoxy) phenyl)-6,7-(benzo-9-crown-3)-4-quinazolinamine The synthetic route is as follows:

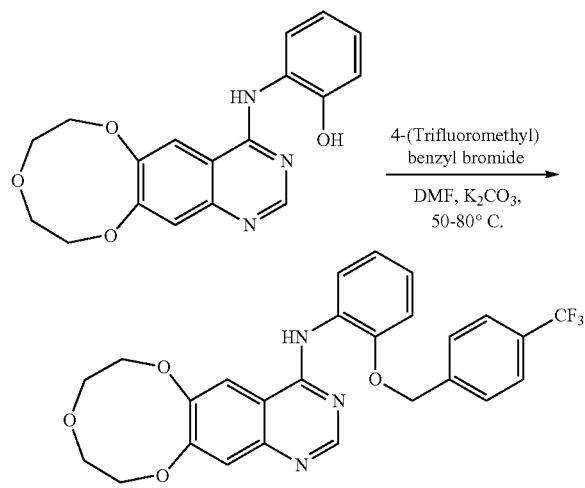

100 mg of N-(2-hydroxyphenyl)-6,7-(benzo-9-crown-3)-4-quinazolinamine (0.3 mmol), 250 mg (1.8 mmol) of potassium carbonate, 16 mg (0.06 mmol) of 18-crown-6, and 5 mg (0.03 mmol) of KI was sequentially added to 2.5 mL of DMF, stirred at 35° C. for 0.5 h, then added with 96 mg (0.4 mmol) of 4-(trifluoromethyl)benzyl bromide, and stirred for 6 h. The completion of the reaction was monitored by TLC. After the reaction was cooled to room temperature, the reaction liquid was poured into ice water, extracted with CH$_2$Cl$_2$, and the organic phase was collected and washed with saturated sodium bicarbonate, water and saturated sodium chloride sequentially and dried over anhydrous sodium sulfate. After the solvent was rotary evaporated, 23 mg of pale yellow solid was obtained by column chromatography (petroleum ether:ethyl acetate=1:1) in a yield of 15%, m.p. 115-116° C.

$^1$H NMR (400 MHz, DMSO-d$_6$): δ 9.24 (s, 1H, —NH), 8.35 (s, 1H, ArH), 8.10 (s, 1H, ArH), 7.64 (m, 2H, ArH), 7.58 (m, 3H, ArH), 7.27 (s, 1H, ArH), 7.22 (m, 1H, ArH), 7.12 (m, 1H, ArH), 7.03 (m, 1H, ArH), 5.27 (s, 2H, —CH$_2$), 4.56 (brs, 2H, —CH$_2$), 4.38 (brs, 2H, CH$_2$), 3.87 (brs, —CH$_2$). $^{33}$CNMR (100 MHz, DMSO-d$_6$): δ 157.76, 15684, 154.06, 152.25, 151.45, 147.33, 142.11, 127.82, 127.36, 127.30, 127.30, 127.30, 126.42, 125.04, 125.00, 120.78, 117.73, 115.02, 113.27, 110.93, 74.86, 74.86, 72.82, 71.87, 71.34, 68.60. MS (ESI+) m/z: 498.36 [M−H]$^+$ Example 8

Synthesis of N-(3-((4-trifluoromethylphenyl)methoxy) phenyl)-6,7-(benzo-9-crown-3)-4-quinazolinamine N-(3-hydroxyphenyl)-6,7-(benzo-9-crown-3)-4-quinazolinamine was firstly synthesized in steps 8.1-8.7. Steps 8.1-8.7 were the similar as steps 1.1-1.7 in Example 1, except that o-aminophenol was replaced with 3-aminophenol as starting material.

8.8 Synthesis of N-(3-((4-trifluoromethylphenyl)methoxy) phenyl)-6,7-(benzo-9-crown-3)-4-quinazolinamine The synthesis procedure was similar to that in step 7.8 of Example 7, except that N-(2-hydroxyphenyl)-6,7-(benzo-9-crown-3)-4-quinazolinamine was replaced with N-(3-hydroxyphenyl)-6,7-(benzo-9-crown-3)-4-quinazolinamine as starting material. The product was obtained as white solid in a yield of 16%, m.p. 206-207° C.

$^1$H NMR (400 MHz, DMSO-d6): δ 9.56 (s, 1H, —NH), 8.47 (s, 1H, ArH), 8.30 (s, 1H, ArH), 7.74 (m, 6H, ArH), 7.49 (d, J=7.40 Hz, 1H, ArH), 7.29 (s, 2H, ArH), 6.77 (d, J=7.48 Hz, 1H, ArH), 5.26 (s, 2H, 4.58 (s, 2H, —CH$_2$), 4.42 (s, 2H, —CH$_2$), 3.87 (s, 4H, —CH$_2$). $^{13}$C NMR (100 MHz, DMSO-d6): δ 158.05, 156.85, 156.58, 153.57, 151.52, 147.45, 142.05, 140.72, 129.11, 128.39, 127.94, 125.55, 125.28, 125.24, 122.84, 117.66, 115.46, 114.51, 111.14, 109.36, 108.61, 74.98, 72.68, 71.87, 71.31, 68.30. MS (ESI+) m/z: 498.1 [M−H]$^+$

Example 9

Synthesis of N-(4-((4-trifluoromethylphenyl)methoxy) phenyl)-6,7-(benzo-9-crown-3)-4-quinazolinamine N-(4-hydroxyphenyl)-6,7-(benzo-9-crown-3)-4-quinazolinamine was firstly synthesized in steps 9.1-9.7. Steps 9.1-9.7 were similar as steps 1.1-1.7 in Example 1, except that o-aminophenol was replaced with 4-aminophenol as starting material.

9.8 Synthesis of N-(4-((4-trifluoromethylphenyl) methoxy) phenyl)-6,7-(benzo-9-crown-3)-4-quinazolinamine The synthesis procedure was similar to that in step 7.8 of Example 7 except that N-(2-hydroxyphenyl)-6,7-(benzo-9-crown-3)-4-quinazolinamine was replaced with N-(4-hydroxyphenyl)-6,7-(benzo-9-crown-3)-4-quinazolinamine as starting material. The product was obtained as white solid, yield 12%, m.p. 214° C.
$^1$H NMR (400 MHz, DMSO-d6): δ 9.44 (s, 1H, —NH), 8.36 (s, 1H, ArH), 8.17 (s, 1H, ArH), 7.75 (m, 2H, ArH), 7.67 (m, 4H, ArH), 7.23 (s, 1H, ArH), 7.03 (d, J=9.08 Hz, 2H, ArH), 5.22 (s, 2H, —CH$_2$), 4.54 (brs, 2H, —CH$_2$), 4.38 (brs, 2H, —CH$_2$), 3.84 (brs, 4H, —CH$_2$). $^{13}$C NMR (100 MHz. DMSO-d6): δ 156.75, 156.71, 154.26, 153.84, 151.36, 147.32, 142.12, 132.59, 128.36, 128.04, 127.92, 125.55, 125.30, 125.26, 125.22, 123.89, 122.85, 117.68, 115.23, 114.60, 110.94, 74.92, 72.74, 71.84, 71.36, 68.42. MS (ESI+) m/z: 498.40 [M–H]$^+$

Example 10

Synthesis of N-(4-((3-chloro-4-fluorophenyl) methoxy) phenyl)-6,7-(benzo-9-crown-3)-4-quinazolinamine N-(4-hydroxyphenyl)-6,7-(benzo-9-crown-3)-4-quinazolinamine was firstly synthesized in steps 10.1-10.7. Steps 10.1-10.7 were similar as steps 1.1-1.7 in Example 1, except that o-aminophenol was replaced with 4-aminophenol as starting material.

10.8 Synthesis of N-(4-((3-chloro-4-fluorophenyl) methoxy) phenyl)-6,7-(benzo-9-crown-3)-4-quinazolinamine The synthesis procedure was similar to that in step 7.8 of Example 7 except that 4-(trifluoromethyl)benzyl bromide and N-(2-hydroxyphenyl)-6,7-(benzo-9-crown-3)-4-quinazolinamine were replaced with 3-chloro-4-fluorobenzyl chloride and N-(4-hydroxyphenyl)-6,7-(benzo-9-crown-3)-4-quinazolinamine, respectively, as starting materials. The product was obtained as pale yellow solid in a yield of 36%, m.p. 221-222° C.
$^1$H NMR (400 MHz, DMSO-d6): δ 9.62 (s, 1H, —NH), 8.46 (s, 1H, ArH), 8.10 (d, J=4.9 Hz, 2H, ArH), 7.80 (s, 1H, ArH), 7.43 (t, J=9.1 Hz, 1H, ArH), 7.50 (d, J=6.9 Hz, 2H, ArH), 7.20 (s, 1H, ArH), 7.04 (d, J=6.8 Hz, 2H, ArH), 5.16 (s, 2H, —CH2), 4.60 (s, 2H, —CH2), 4.40 (s, 2H, —CH2), 3.87 (s, 4H, —CH2). $^{13}$C NMR (100 MHz, DMSO-d6): δ 156.02, 154.350 (d, J=4.5 Hz, 2H), 153.89, 151.22, 151.90, 147.68, 147.39, 137.20, 1369.69, 132.19, 128.37, 127.60, 127.60, 123.89, 123.89, 117.76, 115.20, 114.61, 114.61, 111.00, 75.21, 73.01, 71.92, 71.51, 69.58. MS (ESI+) m/z: 494.76 [M–H]$^+$

Example 11

Synthesis of N-(2-((4-pyridyl) methoxy) phenyl)-6,7-(benzo-9-crown-3)-4-quinazolinamine Steps 11.1-11.7 were completely consistent with steps 1.1-1.7 in Example 1. N-(2-hydroxyphenyl)-6,7-(benzo-9-crown-3)-4-quinazoline was firstly synthesized in steps 11.1-11.7.

11.8 Synthesis of N-(2-((4-pyridyl) methoxy) phenyl)-6,7-(benzo-9-crown-3)-4-quinazolinamine The synthesis procedure was similar to that in step 7.8 in Example 7, except that 4-(trifluoromethyl)benzyl bromide was replaced with 4-pyridylmethyl chloride as starting material. Pale yellow solid was obtained (yield: 33%, m.p. 231-232° C.).
$^1$HNMR (400 MHz, DMSO-d 6): δ 9.29 (s, 1H, —NH), 8.39 (s, 1H, ArH), 8.16 (s, 1H, ArH), 8.14 (d, J=5.8 Hz, 2H, ArH), 7.82 (d, J=7.0 Hz, 2H, ArH), 7.58 (d, J=7.5 Hz, 1H, ArH), 7.30 (s, 1H, ArH), 7.24 (brs, 1H, ArH), 7.12 (d, J=8.1 Hz, 1H, ArH), 7.10 (d, J=7.5 Hz, 1H, ArH), 5.32 (s, 2H, —CH$_2$), 4.60 (brs, 2H, —CH$_2$), 4.39 (brs, 2H, —CH$_2$), 3.91 (brs, 4H, —CH$_2$) NMR (100 MHz, DMSO-d 6): δ 157.60, 156.81, 154.00, 152.16, 151.39, 147.31, 145.32, 135.63, 128.09, 127.86, 127.59, 126.76, 126.22, 120.05, 117.75, 114.91, 11.2.35, 74.88, 72.85, 71.86, 71.37, 68.45. MS (ESI+) m/z: 431.36 [M–H]$^+$

Example 12

Synthesis of N-(3-((phenyl) methoxy) phenyl)-6,7-(benzo-9-crown-3)-4-quinazolinamine N-(3-hydroxyphenyl)-6,7-(benzo-9-crown-3)-4-quinazolinamine was firstly synthesized in steps 12.1-12.7. Steps 12.1-12.7 were similar as steps 1.1-1.7 in Example 1, except that o-aminophenol was replaced with 3-aminophenol as starting material.

12.8 Synthesis of N-(3-((phenyl) methoxy) phenyl)-6,7-(benzo-9-crown-3)-4-quinazolinamine The synthesis procedure was similar to that in Step 7.8 of Example 7 except that 4-(trifluoromethyl)benzyl bromide and N-(2-hydroxyphenyl)-6,7-(benzo-9-crown-3)-4-quinazolinamine were replaced with benzyl chloride and N-(3-hydroxyphenyl)-6,7-(benzo-9-crown-3)-4-quinazolinamine, respectively, as starting materials. The synthesis method was similar as in Example 7. The product was obtained as 50.4 mg of pale yellow solid in a yield of 39%, m.p. 223-214° C.
$^1$H NMR (400 MHz, DMSO-d6): δ 9.47 (s, 1H, —NH), 8.48 (s, 1H, ArH), 8.25 (s, 1H, ArH), 7.71 (s, 1H, ArH), 7.47 (t, J=7.2 Hz, 3H, ArH), 7.41 (t, J=7.2 Hz, 2H, ArH), 7.35 (d, J=7.2 Hz, 1H, ArH), 7.28 (t, J=5.5 Hz, 2H, ArH), 6.77 (dd, J=8.1 Hz, 1H, ArH), 5.13 (s, 2H, —CH$_2$), 4.57 (brs, 2H, —CH$_2$). 4.42 (brs, 2H, —CH$_2$), 3.87 (brs, 4H, —CH$_2$). $^{13}$C NMR (100 MHz, DMSO-d6): δ 158.42, 156.92, 156.54, 153.62, 151.50, 147.48, 140.60, 137.10, 129, 10, 128.38, 128.38, 127.76, 127.64, 127.64, 117.82, 115.18, 114.24, 111.12, 109.42, 108.57, 74.92, 72.83, 71.79, 71.38, 69.22. MS (ESI+) m/z: 430.1 [M–H]$^+$

Example 13

Synthesis of N-(4-((phenyl) methoxy) phenyl)-6,7-(benzo-9-crown-3)-4-quinazolinamine N-(4-hydroxyphenyl)-6,7-(benzo-9-crown-3)-4-quinazolinamine was firstly synthesized in steps 13.1-13.7. Steps 13.1-13.7 were similar as steps 1.1-1.7 in Example 1, except that o-aminophenol was replaced with 4-aminophenol as starting material.

13.8 Synthesis of N-(4-((phenyl) methoxy) phenyl)-6,7-(benzo-9-crown-3)-4-quinazolinamine The synthesis procedure was similar to that in Step 7.8 of Example 7 except that 4-(trifluoromethyl)benzyl bromide and N-(2-hydroxyphenyl)-6,7-(benzo-9-crown-3)-4-quinazolinamine were replaced with benzyl chloride and N-(4-hydroxyphenyl)-6,7-(benzo-9-crown-3)-4-quinazolinamine, respectively, as starting materials. The product was obtained as pale yellow solid in a yield of 39%, m.p. 229-230° C.

$^1$H NMR (400 MHz, DMSO-d$_6$): δ 9.44 (s, 1H, —NH), 8.39 (s, 1H, ArH), 8.19 (s, 1H, ArH), 7.69 (d, J=6.9 Hz, 2H, ArH), 7.46 (s, 2H, ArH), 7.41 (s, 2H, ArH), 7.35 (s, 1H, ArH), 7.26 (s, 1H, ArH), 7.04 (d, J=6.8 Hz, 2H, ArH), 5.12 (s, 2H, —CH$_2$), 4.56 (s, 2H, —CH$_2$), 4.40 (s, 2H, —CH$_2$), 3.87 (s, 4H, —CH$_2$). $^{13}$CNMR (100 MHz, DMSO-d$_6$): δ 156.76, 154.65, 153.87, 151.34, 147.37, 147.37, 137.19, 132.19, 128.37, 128.37, 127.73, 127.60, 127.60, 123.89, 123.89, 117.76, 115.20, 114.61, 114.61, 111.00, 74.93, 72.82, 71.83, 71.40, 69.38. MS (ESI+) m/z: 430.0 [M−H]$^{30}$

Example 14

Synthesis of N-(2-((4-nitrophenyl) methoxy) phenyl)-6,7-(benzo-12-crown-4)-4-quinazolinamine N-(2-hydroxyphenyl)-6,7-(benzo-12-crown-4)-4-quinazolinamine was firstly synthesized in steps 14.1-14.7. Steps 14.1-14.7 were similar as steps 1.1-1.7 in Example 1, except that 4-chloro-6,7-(benzo-9-crown-3)-4-quinazoline was replaced with 4-chloro-6,7-(benzo-12-crown-4)-4-quinazoline as starting material.

14.8 Synthesis of N-(2-((4-nitrophenyl) methoxy) phenyl)-6,7-(benzo-12-crown-4)-4-quinazolinamine The synthesis procedure was similar to that in Step 7.8 of Example 7 except that N-(2-hydroxyphenyl)-6,7-(benzo-9-crown-3)-4-quinazolinamine was replaced with N-(2-hydroxyphenyl)-6,7-(benzo-12-crown-4)-4-quinazolinamine as starting material. The product was obtained as off-white solid in a yield of 30%, m.p. 197-198° C.

$^1$H NMR (400 MHz, DMSO-d 6): δ 9.20 (s, 1H, —NH), 8.37 (s, 1H, ArH), 8.12 (d, J=8.5 Hz, 2H, ArH), 8.03 (s, 1H, ArH), 7.62 (d, J=7.9 Hz, 2H, ArH), 7.60 (s, 1H, ArH), 7.28 (s, 1H, ArH), 7.22 (t, J=7.4 Hz, 1H, ArH), 7.12 (d, J=8.0 Hz, 1H, ArH), 7.0511, J=7.5 Hz, 1H, ArH). 5.32 (s, 2H, —CH$_2$), 4.28 (brs, 4H, —CH$_2$), 3.79 (brs, 4H, —CH$_2$), 3.63 (s, brs, 4H, —CH$_2$). $^{13}$C NMR (100 MHz, DMSO-d 6): δ157.89, 155.96, 153.85, 152.38, 149.79, 147.30, 146.91, 145.34, 128.02, 127.75, 127.75, 127.67, 126.68, 123.45, 123.45, 121.14, 113.52, 111.81, 109.99, 109.66, 72.80, 70.60, 70.51, 70.12, 68.86, 68.53, 48.73. MS (ESI+) m/z: 519.4 [M+H]$^+$ Example 15

Synthesis of N-(3-((4-nitrophenyl) methoxy) phenyl)-6,7-(benzo-12-crown-4)-4-quinazolinamine N-(3-hydroxyphenyl)-6,7-(benzo-12-crown-4)-4-quinazolinamine was firstly synthesized in steps 15.1-15.7. Steps 15.1-15.7 were similar as steps 1.1-1.7 in Example 1, except that o-aminophenol and 4-chloro-6,7-(benzo-9-crown-3)-4-quinazoline were replaced with 3-aminophenol and 4-chloro-6,7-(benzo-12-crown-4)-4-quinazoline, respectively, as starting materials.

15.8 Synthesis of N-(3-((4-nitrophenyl) methoxy) phenyl)-6,7-(benzo-12-crown-4)-4-quinazolinamine The synthesis procedure was similar to that in step 7.8 of Example 7 except that N-(2-hydroxyphenyl)-6,7-(benzo-9-crown-3)-4-quinazolinamine was replaced with N-(3-hydroxyphenyl)-6,7-(benzo-12-crown-4)-4-quinazolinamine as starting material. The product was obtained as pale yellow solid in a yield of 23%, m.p. 153-154° C.

$^1$H NMR (400 MHz, DMSO-d 6): δ 9.46 (s, 1H, —NH), 8.48 (s, 1H, ArH), 8.28 (d, J=8.64 Hz, 2H, ArH), 8.17 (s, 1H, ArH), 7.76 (d, J=8.56 Hz, 2H, ArH), 7.72 (s, 1H, ArH), 7.46 (d, J=8.04 Hz, 1H, ArH), 7.29 (s, 2H, ArH), 6.78 (d, J=8.04 Hz, 1H, ArH), 5.31 (s, 2H, —CH$_2$), 4.29 (brs, 4H, —CH$_2$), 3.80 (brs, 2H, —CH$_2$), 3.75 (brs, 2H, —CH$_2$), 3.64 (s, 4H, —CH$_2$). $^{13}$C NMR (100 MHz, DMSO-d 6): δ 158.11, 156:66, 156.07, 153.44, 149.81, 147.69, 147.12, 145.30, 140.94, 129.36, 128.36, 128.36, 123.74, 123.74, 114.87, 111.70, 110.53, 109.89, 109.48, 108.90, 73.09, 70.55, 70.42, 70.06, 68.89, 68.48, 68.20. MS(ESI+) m/z: 519.1 [M+H]$^+$ Example 16

Synthesis of N-(4-((4-nitrophenyl) methoxy) phenyl)-6,7-(benzo-12-crown-4)-4-quinazolinamine N-(4-hydroxyphenyl)-6,7-(benzo-12-crown-4)-4-quinazolinamine was firstly synthesized in steps 16.1-16.7. Steps 16.1-16.7 were similar as steps 1.1-1.7 in Example 1, except that o-aminophenol and 4-chloro-6,7-(benzo-9-crown-3)-4-quinazoline were replaced with 4-aminophenol and 4-chloro-6,7-(benzo-12-crown-4)-4-quinazoline, respectively, as starting materials.

16.8 Synthesis of N-(4-((4-nitrophenyl) methoxy) phenyl)-6,7-(benzo-12-crown-4)-4-quinazolinamine The synthesis procedure was similar to that in Step 7.8 of Example 7 except that N-(2-hydroxyphenyl)-6,7-(benzo-9-crown-3)-4-quinazolinamine was replaced with N-(4-hydroxyphenyl)-6,7-(benzo-12-crown-4)-4-quinazolinamine as starting material; the product was obtained as white solid, yield 36%, m.p. 192° C.

$^1$H NMR (400 MHz, DMSO-d$_6$): δ 9.45 (s, 1H, —NH), 8.39 (s, 1H, ArH), 8.28 (d, J=8.6 Hz, 2H, ArH), 8.19 (s, 1H, ArH), 7.74 (d, J=8.6 Hz, 2H, ArH), 7.71 (d, J=8.9 Hz, 2H, ArH), 7.26 (s, 1H, ArH), 7.06 (d, J=8.9 Hz, 2H, ArH), 5.30 (s, 2H, 4.56 (brs, 2H, —CH$_2$), 4.40 (brs, 2H, —CH$_2$), 3.86 (brs, 4H, —CH$_2$). $^{13}$CNMR (100 MHz, DMSO-d$_6$): δ 156.78, 156.71, 154.14, 153.82, 151.35, 147.35, 146.94, 145.18, 132.73, 128.15, 128.15, 123.88, 123.88, 123.54, 123.54, 117.75, 115.16, 114.67, 114.67, 110.96, 74.91, 72.82, 71.81, 71.39, 68.20. MS (ESI+) m/z 475.1 [M−H]$^+$ Example 17

Synthesis of N-(2-((phenyl) methoxy) phenyl)-6,7-(benzo-12-crown-4)-4-quinazolinamine N-(4-hydroxyphenyl)-6,7-(benzo-12-crown-4)-4-quinazolinamine was firstly synthesized in steps 17.1-17.7. Steps 17.1-17.7 were similar as steps 1.1-1.7 in Example 1, except that 4-chloro-6,7-(benzo-9-crown-3)-4-quinazoline was replaced with 4-chloro-6,7-(benzo-12-crown-4)-4-quinazoline as starting material.

17.8 Synthesis of N-(2-((phenyl) methoxy) phenyl)-6,7-(benzo-12-crown-4)-4-quinazolinamine The synthesis procedure was similar to that in Step 7.8 of Example 7 except that 4-(trifluoromethyl) benzyl bromide and N-(2-hydroxyphenyl)-6,7-(benzo-9-crown-3)-4-quinazolinamine were replaced with benzyl chloride and N-(2-hydroxyphenyl)-6,7-(benzo-12-crown-4)-4-quinazolinamine, respectively, as starting materials; the product was obtained as off-white solid in a yield of 35%, m.p. 150-151° C.

$^1$HNMR (400 MHz, DMSO-d6): δ 9.09 (s, 1H, —NH), 8.36 (s, 1H, ArH), 7.97 (s, 1H, ArH), 7.66 (d, J=6.8 Hz, 1H, ArH), 7.35 (s, 2H, ArH), 7.26 (d, J=5.8 Hz, 4H, ArH), 7.21 (s, 1H, ArH), 7.18 (s, 1H, ArH), 7.02 (s, 1H, ArH), 5.15 (s, 2H, —CH$_2$), 4.28 (s, 2H, —CH$_2$), 4.22 (s, 2H, —CH$_2$), 3.78 (s, 2H, —CH$_2$), 3.74 (s, 2H, —CH$_2$), 3.63 (s, 4H, —CH$_2$). $^{13}$C NMR (100 MHz, DMSO-d6): δ 157.53, 155.71, 153.70, 152.26, 149.57, 147.30, 137.10, 128.17, 128.17, 127.94, 127.54, 126.98, 126.98, 126.83, 126.08, 120.58, 113.25, 111.84, 109.64, 109.58, 72.64, 70.48, 70.40, 70.02, 69.58, 68.69, 68.41. MS (ESI+) m/z: 474.2 [M+H]$^+$

Example 18

Synthesis of N-(3-((phenyl) methoxy) phenyl)-6,7-(benzo-12-crown-4)-4-quinazolinamine N-(3-hydroxyphenyl)-6,7-(benzo-12-crown-4)-4-quinazolinamine was firstly synthesized in steps 18.1-18.7; steps 18.1-18.7 were similar as 1.1-1.7 in Example 1, except that o-aminophenol and 4-chloro-6,7-(benzo-9-crown-3)-4-quinazoline were replaced with 3-aminophenol and 4-chloro-6,7-(benzo-12-crown-4)-4-quinazoline, respectively, as starting materials.

18.8 Synthesis of N-(3-((phenyl) methoxy) phenyl)-6,7-(benzo-12-crown-4)-4-quinazolinamine The synthesis procedure was similar to that in step 7.8 of Example 7 except that 4-(trifluoromethyl) benzyl bromide and N-(2-hydroxyphenyl)-6,7-(benzo-9-crown-3)-4-quinazolinamine were replaced with benzyl chloride and N-(3-hydroxyphenyl)-6,7-(benzo-12-crown-4)-4-quinazolinamine, respectively, as starting materials; the product was obtained as pale yellow solid in a yield of 19%, m.p. 137-138° C.

$^1$H NMR (400 MHz, DMSO-d 6). δ 9.42 (s, 1H, —NH), 8.47 (s, 1H, ArH), 8.14 (s, 1H, ArH), 7.66 (brs, 1H, ArH), 7.47-7.24 (m, 8H, ArH), 6.75 (d, J=7.88 Hz. 1H, ArH), 5.10 (s, 2H, —CH$_2$), 4.27 (brs, 4H, —CH$_2$), 3.77 (brs, 2H, —CH$_2$), 3.72 (brs, 2H, —CH$_2$), 3.61 (s, 4H, —CH$_2$). $^{13}$C NMR (100 MHz, DMSO-d 6): δ58.41, 156.48, 155.87, 153.32, 149.59, 147.59, 140.69, 137.10, 129.08, 128.38, 128.38, 127.76, 127.64, 127.64, 114.33, 111.53, 110.37, 109.72, 109.26, 108.66, 72.92, 70.40, 70.18, 69.87, 69.19, 68.75, 68.31 MS (ESI+) m/z: 474.7 [M+H]$^+$ Example 19

Synthesis of N-(4-((phenyl) methoxy) phenyl)-6,7-(benzo-12-crown-4)-4-quinazolinamine N-(4-hydroxyphenyl)-6,7-(benzo-12-crown-4)-4-quinazolinamine was firstly synthesized in steps 19.1-19.7; steps 19.1-19.7 were similar as steps 1.1-1.7 in Example 1, except that o-aminophenol and 4-chloro-6,7-(benzo-9-crown-3)-4-quinazoline were replaced with 4-aminophenol and 4-chloro-6,7-(benzo-12-crown-4)-4-quinazoline, respectively, as starting materials.

19.8 Synthesis of N-(4-((phenyl) methoxy) phenyl)-6,7-(benzo-12-crown-4)-4-quinazolinamine The synthesis procedure was similar to that in step 7.8 of Example 7 except that 4-(trifluoromethyl) benzyl bromide and N-(2-hydroxyphenyl)-6,7-(benzo-9-crown-3)-4-quinazolinamine were replaced with benzyl chloride and N-(4-hydroxyphenyl)-6,7-(benzo-12-crown-4)-4-quinazolinamine, respectively, as starting materials; the product was obtained as off-white solid in a yield of 32%, m.p. 174-175° C.

$^1$H NMR (400 MHz, DMSO-d 6): δ 9.38 (s, 1H, —NH), 8.40 (s, 1H, ArH), 8.10 (s, 1H, ArH), 7.66 (d, J=8.5 Hz, 2H, ArH), 7.47 (d, J=7.1 Hz, 2H, ArH), 7.41 (t, J=7.1 Hz, 2H, ArH), 7.34 (d, J=6.8 Hz, 1H, ArH), 7.26 (s, 1H, ArH), 7.04 (d, J=8.5 Hz, 2H, ArH), 5.12 (s, 2H, —CH$_2$), 4.28 (s, 4H, —CH$_2$), 3.77 (d, J=16.8 Hz, 2H, —CH$_2$), 3.64 (s, 4H, CH$_2$). $^{13}$C NMR (100 MHz, DMSO-d 6): δ 156.74, 155.72, 154.64, 153.56, 149.47, 147.42, 137.19, 132.42, 128.37, 128.37, 127.73, 127.61, 127.61, 124.03, 124.03, 114.61, 114.61, 111.62, 110.24, 109.53, 72.86, 70.44, 70.25, 69.94, 69.38, 68.77, 68.38. MS (ESI+) m/z: 474.25 [M+H]+

Example 20

Synthesis of N-(2-((phenyl) methoxy) phenyl)-6,7-(benzo-15-crown-5)-4-quinazolinamine N-(4-hydroxyphenyl)-6,7-(benzo-15-crown-5)-4-quinazolinamine firstly was synthesized in steps 20.1-20.7; steps 20.1-20.7 were similar as steps 1.1-1.7 in Example 1, except that 4-chloro-6,7-(benzo-9-crown-3)-4-quinazoline was replaced with 4-chloro-6,7-(benzo-15-crown-5)-4-quinazoline as starting material.

20.8 Synthesis of N-(2-((phenyl) methoxy) phenyl)-6,7-(benzo-15-crown-5)-4-quinazolinamine The synthesis procedure was similar to that of step 7.8 in Example 7, except that 4-(trifluoromethyl)benzyl bromide was replaced with benzyl chloride as starting material; light brown solid was obtained (yield: 18%, m.p. 128-129° C.).

$^1$H NMR (400 MHz, DMSO-d$_6$): δ 9.08 (s, 1H, —NH), 8.36 (s, 1H, ArH), 7.70 (m, 2H, ArH), 7.35 (m, 2H, ArH), 7.26 (m, 3H, ArH), 7.19 (m, 2H, ArH), 7.05 (s, 1H, ArH), 7.03 (m, 1H, ArH), 5.14 (s, 2H, —CH$_2$), 4.21 (brs, 2H, —CH$_2$), 4.12 (brs, 2H, —CH$_2$), 3.84 (brs, 4H, —CH$_2$), 3.66 (s, 4H, —CH$_2$), 3.65 (s, 4H, —CH$_2$). $^{13}$C NMR (100 MHz, DMSO-d$_6$): δ 157.38, 153.79, 153:32, 152.30, 148.28, 146.86, 137.24, 128.34, 128.34, 128.22, 127.74, 127.22, 127.22, 126.78, 126.08, 120.76, 113.31, 108.88, 107.96, 102.81, 70.82, 70.82, 69.73, 69.73, 69.74, 69.74, 68.69, 68.69, 68.32 MS (ESI+) m/z: 518.2 [M+H]$^+$ Example 21

Synthesis of N-(3-((phenyl) methoxy) phenyl)-6,7-(benzo-15-crown-5)-4-quinazolinamine N-(3-hydroxyphenyl)-6,7-(benzo-15-crown-5)-4-quinazolinamine was firstly synthesized in steps 21.1-21.7; steps 21.1-21.7 were similar as steps 1.1-1.7 in Example 1, except that o-aminophenol and 4-chloro-6,7-(benzo-9-crown-3)-4-quinazoline were replaced with 3-aminophenol and 4-chloro-6,7-(benzo-15-crown-5)-4-quinazoline, respectively, as starting materials.

21.8 Synthesis of N-(3-((phenyl) methoxy) phenyl)-6,7-(benzo-15-crown-5)-4-quinazolinamine The synthesis procedure was similar to that in step 7.8 of Example 7 except that 4-(trifluoromethyl) benzyl bromide and N-(2-hydroxyphenyl)-6,7-(benzo-9-crown-3)-4-quinazolinamine were replaced with benzyl chloride and N-(3-hydroxyphenyl)-6,7-(benzo-15-crown-5)-4-quinazolinamine, respectively, as starting materials; the product was obtained as pale yellow solid in a yield of 19%, m.p. 137-138° C.

$^1$H NMR (400 MHz, DMSO-d 6): δ 9.39 (s, 1H, —NH) 8.40 (s, 1H, ArH), 7.98 (s, 1H, ArH), 7.61 (brs, 1H, ArH), 7.46-7.14 (m, 8H, ArH), 6.95 (d, J=7.88 Hz, 1H, ArH), 5.11 (s, 2H, —CH$_2$), 4.21 (brs 4H, —CH$_2$), 3.85 (brs, 2H, —CH$_2$), 3.83 (brs, 2H, —CH$_2$). 3.89 (s, 4H, —CH$_2$), 3.68 (s, 4H, —CH$_2$). $^{13}$C NMR (100 MHz, DMSO-d 6): δ157.91, 155.66, 154.23, 153.69, 150.22, 147.46, 140.88, 137.02, 128.94, 128.55, 127.89, 127.56, 127.22, 127.12, 114.75, 111.21, 110.18, 109.32, 109.26, 108.35, 71.02, 70.43, 69.98, 69.58, 69.02, 69.00, 68.66, 68.27, 68.05, MS (ESI+) m/z: 518.86 [M+H]$^+$ Example 22

Synthesis of N-(2-((4-trifluoromethylphenyl)methoxy) phenyl)-6,7-(benzo-12-crown-4)-4-quinazolinamine N-(2-hydroxyphenyl)-6,7-(benzo-12-crown-4)-4-quinazolinamine was firstly synthesized in steps 22.1-22.7. Steps 22.1-22.7 were similar as steps 1.1-1.7 in Example 1, except that 4-chloro-6,7-(benzo-9-crown-3)-4-quinazoline was replaced with 4-chloro-6,7-(benzo-12-crown-4)-4-quinazoline as starting material.

22.8 Synthesis of N-(2-((4-trifluoromethylphenyl)methoxy) phenyl)-6,7-(benzo-12-crown-4)-4-quinazolinamine The synthesis procedure was similar to that in Step 7.8 of Example 7 except that N-(2-hydroxyphenyl)-6,7-(benzo-9-crown-3)-4-quinazolinamine was replaced with N-(2-hydroxyphenyl)-6,7-(benzo-12-crown-4)-4-quinazolinamine as starting material; the product was obtained as pale yellow solid in a yield of 15%, m.p. 181-182° C.

$^1$H NMR (400 MHz, DMSO-d$_6$): δ 9.18 (s, 1H, —NH), 8.37 (s, 1H, ArH), 8.02 (s, 1H, ArH), 7.61 (m, 5H, ArH), 7.28 (s, 1H, ArH), 7.22 (m, 1H, ArH), 7.13 (m, 1H, ArH), 7.03 (m, 1H, ArH), 5.27 (s, 2H, —CH$_2$), 4.29 (brs, 2H, —CH$_2$), 4.25 (brs, 2H, —CH$_2$), 3.78 (brs, 2H, —CH$_2$), 3.74 (brs, 2H, —CH$_2$), 3.63 (s, 4H, —CH$_2$). $^{13}$C NMR (100 MHz, DMSO-d$_6$): δ 158.15, 156.22, 154.19, 152.69, 150.06, 147.73, 142.57, 128.94, 128.66, 128.3, 128.34, 127.80, 126.84, 125.51, 125.47, 123.27, 121.29, 113.71, 112.22, 110.27, 110.01, 73.08, 70.90, 70.80, 70.43, 69.15, 69.07, 68.84. MS (ESI+) m/z: 542.41 [M+H]$^+$ Example 23

Synthesis of N-(3-((4-trifluoromethylphenyl)methoxy) phenyl)-6,7-(benzo-12-crown-4)-4-quinazolinamine Structural formula of N-(3-((4-trifluoromethylphenyl)methoxy) phenyl)-6,7-(benzo-12-crown-4)-4-quinazolinamine is as follows:

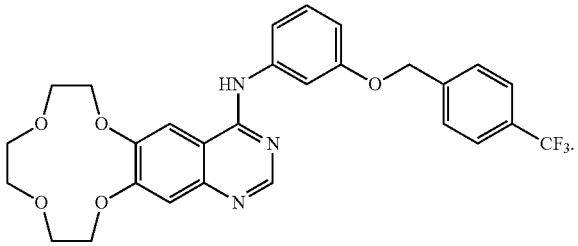 [SMILES: FC(F)(F)c1ccc(COc2cccc(Nc3ncnc4cc5c(cc34)OCCOCCOCCO5)c2)cc1]

N-(3-hydroxyphenyl)-6,7-(benzo-12-crown-4)-4-quinazolinamine was firstly synthesized in steps 23.1-23.7. Steps 23.1-23.7 were similar as steps 1.1-1.7 in Example 1, except that o-aminophenol and 4-chloro-6,7-(benzo-9-crown-3)-4-quinazoline were replaced with 3-aminophenol and 4-chloro-6,7-(benzo-12-crown-4)-4-quinazoline, respectively, as starting materials.

23.8 Synthesis of N-(3-((4-trifluoromethylphenyl)methoxy) phenyl)-6,7-(benzo-12-crown-4)-4-quinazolinamine The synthesis procedure was similar to that in step 7.8 of Example 7 except that N-(2-hydroxyphenyl)-6,7-(benzo-9-crown-3)-4-quinazolinamine was replaced with N-(3-hydroxyphenyl)-6,7-(benzo-12-crown-4)-4-quinazolinamine as starting material; the product was obtained as pale yellow solid in a yield of 17%, m.p. 167-168° C.

$^1$H NMR (400 MHz, DMSO-d$_6$): δ 9.48 (s, 1H, —NH), 8.45 (s, 1H, ArH), 8.18 (s, 1H, ArH) 7.76 (m, 2H, ArH), 7.68 (m, 3H, ArH), 7.44 (d, J=8.08 Hz, 1H, ArH), 7.26 (m, 2H, ArH), 6.75 (d, J=8.16 Hz, 1H, ArH), 5.23 (s, 2H, —CH$_2$), 4.27 (brs, 4H, —CH$_2$), 3.77 (brs, 2H, —CH$_2$), 3.72 (brs, 2H, —CH$_2$), 3.61 (s, 4H, —CH$_2$) $^{13}$C NMR (100 MHz, DMSO-d$_6$): δ 158.07, 156.50, 155.84, 153.25, 149.60, 147.56, 142.08, 140.83, 129.10, 128.07, 127.94, 127.94, 125.56, 125.29, 125.25, 114.58, 111.59, 110.43, 109.79, 109.25, 108.71, 72.89, 70.37, 70.26, 69.90, 68.72, 68.30, 68.30. MS (ESI+) m/z: 542.38 [M+H]$^+$ Example 24

Synthesis of N-(4-((4-trifluoromethylphenyl)methoxy) phenyl)-6,7-(benzo-12-crown-4)-4-quinazolinamine N-(4-hydroxyphenyl)-6,7-(benzo-12-crown-4)-4-quinazolinamine was firstly synthesized by steps 24.1-24.7; steps 24.1-24.7 were similar as steps 1.1-1.7 in Example 1, except that o-aminophenol and 4-chloro-6,7-(benzo-9-crown-3)-4-quinazoline were replaced with 4-aminophenol and 4-chloro-6,7-(benzo-12-crown-4)-4-quinazoline, respectively, as starting materials.

24.8 Synthesis of N-(4-((4-trifluoromethylphenyl)methoxy) phenyl)-6,7-(benzo-12-crown-4)-4-quinazolinamine The synthesis procedure was similar to that in Step 7.8 of Example 7 except that N-(2-hydroxyphenyl)-6,7-(benzo-9-crown-3)-4-quinazolinamine was replaced with N-(4-hydroxyphenyl)-6,7-(benzo-12-crown-4)-4-quinazolinamine as starting material; the product was obtained as white solid in a yield of 17%, m.p. 185-186° C.

$^1$H NMR (400 MHz, DMSO-d$_6$) δ 9.40 (s, 1H, —NH), 8.40 (s, 1H, ArH), 8.11 (s, 1H, ArH), 7.78 (m, 2H, ArH), 7.69 (m, 3H, ArH), 7.26 (s, 1H, ArH), 7.06 (d, J=9.04 Hz, 2H, ArH), 5.25 (s, 2H, —CH$_2$), 4.28 (brs, 4H, —CH$_2$), 3.79 (brs, 2H, —CH$_2$), 3.75 (brs, 2H, —CH$_2$), 3.64 (s, 4H, —CH$_2$). $^{13}$C NMR (100 MHz, DMSO-d$_6$): δ 156.90, 155.9, 154.45, 153.70, 149.66, 149.66, 147.57, 142.32, 132.85, 128.10, 128.10, 125.47, 125.44, 124.21, 124.21, 114.81, 114.81, 111.78, 110.44, 109.72, 73.03, 70.60, 70.44, 70.11, 68.93, 68.65, 68.54, 48.73. MS (ESI+) m/z: 542.9 [M+H]$^+$ Example 25

Synthesis of N-(3-((4-nitrophenyl) methoxy) phenyl)-6,7-(benzo-15-crown-5)-4-quinazolinamine Structural formula of N-(3-((4-nitrophenyl) methoxy) phenyl)-6,7-(benzo-15-crown-5)-4-quinazolinamine is as follows:

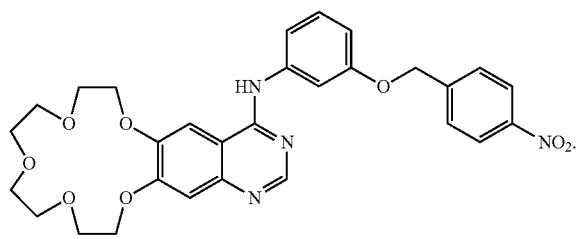 [SMILES: O=[N+]([O-])c1ccc(COc2cccc(Nc3ncnc4cc5c(cc34)OCCOCCOCCOCCO5)c2)cc1]

N-(3-hydroxyphenyl)-6,7-(benzo-15-crown-5)-4-quinazolinamine was firstly synthesized in steps 25.1-25.7. Steps 25.1-25.7 were similar as steps 1.1-1.7 in Example 1, except that o-aminophenol and 4-chloro-6,7-(benzo-9-crown-3)-4-quinazoline were replaced with 3-aminophenol and 4-chloro-6,7-(benzo-15-crown-5)-4-quinazoline, respectively, as starting materials.

25.8 Synthesis of N-(3-((4-nitrophenyl) methoxy) phenyl)-6,7-(benzo-15-crown-5)-4-quinazolinamine The synthesis procedure was similar to that in Step 7.8 of Example 7 except that 4-(trifluoromethyl)benzyl bromide and N-(2-hydroxyphenyl)-6,7-(benzo-9-crown-3)-4-quinazolinamine were replaced with 4-nitrobenzyl chloride and N-(3-hydroxyphenyl)-6,7-(benzo-15-crown-5)-4-quinazolinamine, respectively, as starting materials; the product was obtained as a yellow solid, yield 21%, m.p. 136-137° C.

$^1$H NMR (400 MHz, DMSO-d$_6$): δ 9.51 (s, 1H, —NH), 8.46 (s, 1H, ArH), 8.28 (d, J=8.60 Hz 2H, ArH), 7.95 (s, 1H, ArH), 7.76 (d, J=8.56 Hz, 2H, ArH), 7.72 (s, 1H, ArH), 7.46 (d, J=8.36 Hz, 1H, ArH), 7.30 (t, J=8.16 Hz, 1H, ArH), 7.17 (s, 1H, ArH), 6.78 (d, J=8.12 Hz, 1H, ArH), 5.31 (s, 2H, —CH$_2$), 4.26 (brs, 2H, —CH$_2$), 4.22 (brs, 2H, —CH$_2$). 3.87 (brs, 2H, —CH$_2$), 3.84 (brs, 2H, —CH$_2$), 3.66 (s, 8H, —CH$_2$). $^{13}$C NMR (100 MHz, DMSO-d$_6$): δ 157.87, 156.26, 153.54, 152.71, 148.03, 146.94, 146.87, 145.10, 140.95, 129.04, 128.11, 128.11, 123.49, 123.49, 114.80, 109.07, 109.07, 108.84, 107.78, 103.57, 70.25, 69.20, 69.13, 68.78, 68.27, 68.12, 68.04, 68.00, 67.87. MS (ESI+) m/z: 563.5 [M+H]$^+$ Example 26

Synthesis of N-(4-((4-nitrophenyl) methoxy) phenyl)-6,7-(benzo-15-crown-5)-4-quinazolinamine N-(4-hydroxyphenyl)-6,7-(benzo-15-crown-5)-4-quinazolinamine was firstly synthesized in steps 26.1-26.7; steps 26.1-26.7 were similar as steps 1.1-1.7 in Example 1, except that o-aminophenol and 4-chloro-6,7-(benzo-9-crown-3)-4-quinazoline was replaced with 4-aminophenol and 4-chloro-6,7-(benzo-15-crown-5)-4-quinazoline, respectively, as starting material.

26.8 Synthesis of N-(4-((4-nitrophenyl) methoxy) phenyl)-6,7-(benzo-15-crown-5)-4-quinazolinamine The synthesis procedure was similar to that in step 7.8 of Example 7 except that 4-(trifluoromethyl)benzyl bromide and N-(2-hydroxyphenyl)-6,7-(benzo-9-crown-3)-4-quinazolinamine were replaced with 4-nitrobenzyl chloride and N-(4-hydroxyphenyl)-6,7-(benzo-15-crown-5)-4-quinazolinamine, respectively, as starting materials; the product was obtained as white solid in a yield of 16%, m.p. 209-210° C.

$^1$H NMR (400 MHz, DMSO-d 6): δ 9.42 (s, 1H, —NH), 8.38 (s, 1H, ArH), 8.28 (d, J=8.60 Hz, 2H, ArH), 7.87 (s, 1H, ArH), 7.75 (d, J=8.56 Hz, 2H, ArH), 7.67 (d, J=8.88 Hz, 2H, ArH), 7.14 (s, 1H, ArH), 7.07 (d, J=8.92 Hz, 2H, ArH), 5.30 (s, 2H, —CH$_2$), 4.21 (brs, 4H, —CH$_2$), 3.87 (brs, 2H, —CH$_2$), 3.84 (brs, 2H, —CH$_2$), 3.65 (brs, 8H, —CH$_2$). $^{13}$C NMR (100 MHz, DMSO-d 6): δ 156.49, 154.07, 153.54, 152.96, 148.04, 146.91, 146.76, 145.20, 132.85, 128.15, 128.15, 124.15, 124.15, 123.54, 123.54, 114.61, 114.61, 108.73, 107.79, 103.25, 70.53, 69.44, 69.35, 68.74, 68.44, 68.37, 68.31, 68.17, 68.02. MS (ESI+) m/z: 563.7 [M+H]$^+$ Example 27

Synthesis of N-(4-((phenyl) methoxy) phenyl)-6,7-(benzo-15-crown-5)-4-quinazolinamine N-(4-hydroxyphenyl)-6,7-(benzo-15-crown-5)-4-quinazolinamine was firstly synthesized in steps 27.1-27.7; steps 27.1-27.7 were similar as steps 1.1-1.7 in Example 1, except that o-aminophenol and 4-chloro-6,7-(benzo-9-crown-3)-4-quinazoline were replaced with 4-aminophenol and 4-chloro-6,7-(benzo-15-crown-5)-4-quinazoline, respectively, as starting materials.

27.8 Synthesis of N-(4-((phenyl) methoxy) phenyl)-6,7-(benzo-15-crown-5)-4-quinazolinamine The synthesis procedure was similar to that in Step 7.8 of Example 7 except that 4-(trifluoromethyl) benzyl bromide and N-(2-hydroxyphenyl)-6,7-(benzo-9-crown-3)-4-quinazolinamine were replaced with benzyl chloride and N-(4-hydroxyphenyl)-6,7-(benzo-15-crown-5)-4-quinazolinamine, respectively, as starting materials; the product was obtained as pale yellow solid in a yield of 21%, m.p. 215-216° C.

$^1$H NMR (400 MHz, DMSO-d$_6$): δ 9.36 (s, 1H, —NH), 8.38 (s, 1H, ArH), 7.83 (s, 1H, ArH), 7.63 (d, J=8.96 Hz, 2H, ArH), 7.48 (m, 2H, ArH), 7.41 (m, 2H, 7.35 (m, 1H, ArH), 7.14 (s, 1H, ArH), 7.04 (d, J=8.96 Hz, 2H, ArH), 5.12 (s, 2H, —CH$_2$), 4.21 (brs, 4H, —CH$_2$), 3.87 (brs, 2H, —CH$_2$), 3.83 (brs, 2H, —CH$_2$), 3.66 (s, 4H, —CH$_2$), 3.65 (s, 4H, —CH$_2$), $^{13}$C NMR (100 MHz, DMSO-d$_6$): δ 156.71, 154.79, 153.78, 153.18, 148.29, 146.93, 137.35, 132.63, 128.55, 128.55, 127.92, 127.80, 127.80, 124.36, 124.36, 114.76, 114.76, 108.89, 107.96, 103.29, 70.76, 70.76, 69.69, 69.60, 69.55, 68.96, 68.68, 68.53, 68.25. MS (ESI+) m/z: 518.8[M+H]$^+$

Example 28

Synthesis of N-(3-((4-trifluoromethylphenyl) methoxy) phenyl)-6,7-(benzo-15-crown-5)-4-quinazolinamine N-(3-hydroxyphenyl)-6,7-(benzo-15-crown-5)-4-quinazolinamine was firstly synthesized in steps 28.1-28.7; steps 28.1-28.7 were similar as steps 1.1-1.7 in Example 1, except that o-aminophenol and 4-chloro-6,7-(benzo-9-crown-3)-4-quinazoline were replaced with 3-aminophenol and 4-chloro-6,7-(benzo-15-crown-5)-4-quinazoline, respectively, as starting materials.

28.8 Synthesis of N-(3-((4-trifluoromethylphenyl) methoxy) phenyl)-6,7-(benzo-15-crown-5)-4-quinazolinamine The synthesis procedure was similar to that in step 7.8 of Example 7 except that N-(2-hydroxyphenyl)-6,7-(benzo-9-crown-3)-4-quinazolinamine was replaced with N-(3-hydroxyphenyl)-6,7-(benzo-15-crown-5)-4-quinazolinamine as starting material; the product was obtained as white solid in a yield of 16%, m.p. 143-144° C.

$^1$H NMR (400 MHz, DMSO-d$_6$): δ 9.41 (s, 1H, —NH), 8.43 (s, 1H, ArH), 7.86 (s, 1H, ArH), 7.71 (m, 5H, ArH), 7.40 (d, J=8.8 Hz, 1H, ArH), 7.27 (t, J=8.0 Hz, 1H, ArH), 7.14 (s, 1H, ArH), 6.75 (d, J=8.4 Hz, 1H, ArH), 5.23 (s, 2H, —CH$_2$), 4.20 (brs, 4H, —CH$_2$), 3.85 (brs, 2H, —CH$_2$), 3.82 (brs, 2H, —CH$_2$), 3.63 (s, 8H, —CH$_2$). $^{13}$C NMR (100 MHz, DMSO-d$_6$): δ 158.27, 156.38, 152.92, 152.89, 148.42, 147.15, 142.26, 140.99, 129.32, 128.55, 128.10, 125.74, 125.49, 125.46, 123.04, 114.85, 109.37, 109.11, 109.01, 107.99, 103.28, 70.77, 70.73, 69.66, 69.57, 68.99, 68.65, 68.50, 68.45, 68.27. MS (ESI+) m/z: 586.46 [M+H]$^+$

Example 29

Synthesis of N-(4-((4-trifluoromethylphenyl) methoxy) phenyl)-6,7-(benzo-15-crown-5)-4-quinazolinamine Structural formula of N-(4-((4-trifluoromethylphenyl) methoxy) phenyl)-6,7-(benzo-15-crown-5)-4-quinazolinamine is as follows:

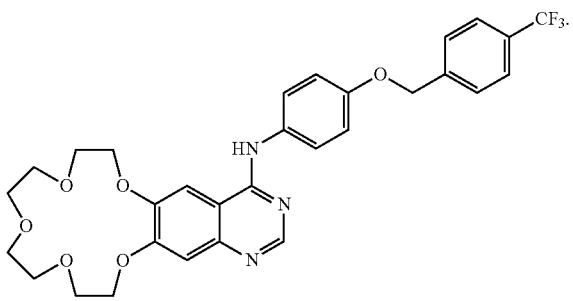 [SMILES: FC(F)(F)c1ccc(COc2ccc(Nc3ncnc4cc5c(cc34)OCCOCCOCCOCCO5)cc2)cc1]

N-(4-hydroxyphenyl)-6,7-(benzo-15-crown-5)-4-quinazolinamine was firstly synthesized in steps 29.1-29.7; steps 29.1-29.7 were similar as steps 1.1-1.7 in Example 1, except that o-aminophenol and 4-chloro-6,7-(benzo-9-crown-3)-4-quinazoline were replaced with 4-aminophenol and 4-chloro-6,7-(benzo-15-crown-5)-4-quinazoline, respectively, as starting materials.

29.8 Synthesis of N-(4-((4-trifluoromethylphenyl) methoxy) phenyl)-6,7-(benzo-15-crown-5)-4-quinazolinamine The synthesis procedure was similar to that in Step 7.8 of Example 7 except that N-(2-hydroxyphenyl)-6,7-(benzo-9-crown-3)-4-quinazolinamine was replaced with N-(4-hydroxyphenyl)-6,7-(benzo-15-crown-5)-4-quinazolinamine as starting material; the product was obtained as pale yellow solid in a yield of 16%, m.p. 197-198° C.

$^1$H NMR (400 MHz, DMSO-d$_6$): δ 9.34 (s, 1H, —NH), 8.36 (s, 1H, ArH), 7.82 (s, 1H, ArH), 7.75 (m, 2H, ArH), 7.65 (m, 3H, ArH), 7.11 (s, 1H, ArH), 7.04 (d, J=9.00 Hz, 2H, ArH), 5.22 (s, 2H, —CH$_2$), 4.18 (brs, 4H, —CH$_2$), 3.85 (brs, 2H, —CH$_2$), 3.81 (brs, 2H, —CH$_2$), 3.63 (s, 8H, —CH$_2$). $^{13}$C NMR (100 MHz, DMSO-d$_6$): δ 156.67, 154.43, 153.80, 153.14, 148.29, 148.29, 146.93, 142.32, 132.88, 128.11, 128.11, 125.47, 125.44, 124.36, 124.36, 114.80, 114.80, 108.87, 107.98, 103.32, 70.78, 69.72, 69.72, 69.63, 69.63, 68.97, 68.97, 68.63, 68.29, 68.29. MS (ESI+) m/z: 586.8 [M+H]$^+$

Example 30

Synthesis of 2-(3-Fluoro-benzyloxy)-5-(7,8,10,11-tetrahydro-6,9,12-trioxa-1,3-diaza-cyclonona[b] naphthalen-4-ylamino)-benzonitrile Structural formula of 2-(3-Fluoro-benzyloxy)-5-(7,8,10,11-tetrahydro-6,9,12-trioxa-1,3-diaza-cyclonona[b]naphthalen-4-ylamino)-benzonitrile is as follows:

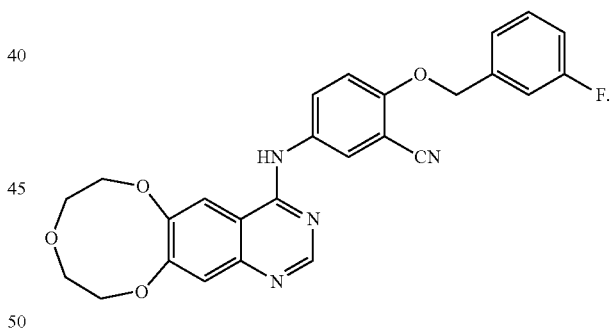

Steps 30.1-30.7 were similar with the steps 1.1-1.7 in Example 1.

In the target compound of Example 30 represented by formula (I), n=0, R=CN; and ArCH$_2$XC$_6$H$_3$RN— is 3-(((3-FC$_6$H$_4$)CH$_2$O)C$_6$H$_3$CN)N—.

The synthesis method for the compound of example 30 is as follows.

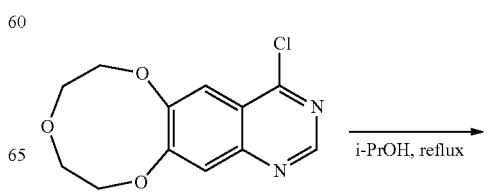

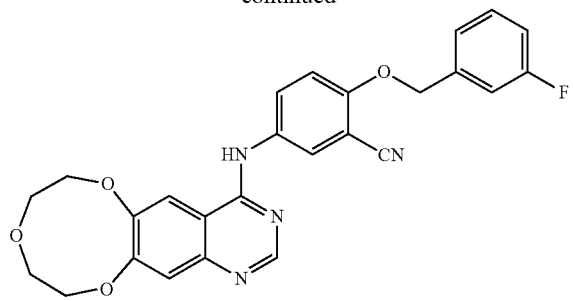

Into a 100 mL eggplant-shaped flask, 4-chloro-6,7-(benzo-9-crown-3) quinazoline (20 mmol) and isopropanol (15 mL) were sequentially added, heated to dissolve, and then 3-cyano-4-(3-fluorobenzyloxy) aniline (30 mmol) was added. The reaction mixture was heated to reflux. After reacting for about 2 h, yellow solid appeared, and the reaction was continued for 2 h. The completion of the reaction was monitored by TLC. The reaction solution was allowed to stand for cooling and then filtered with suction to give 0.22 g of pale yellow solid (yield: 28%) with a melting point of 220-222° C. $^1$H NMR (400 MHz, DMSO-d6) δ 11.34 (d, J=23.6 Hz, 1H), 8.87 (s, 1H), 8.73 (d, J=9.3 Hz, 1H), 7.99 (d, J=2.5, 0.8 Hz, 1H), 7.78-7.66 (m, 1H), 7.54 (td, J=8.0, 6.0 Hz, 1H), 7.46 (d, J=2.9 Hz, 1H), 7.42-7.36 (m, 3H), 7.27 (dd, J=8.9, 2.1 Hz, 1H), 5.36 (s, 2H), 4.91-4.76 (m, 2H), 4.55-4.43 (m, 2H), 3.94 (dd, J=8.6, 5.7 Hz, 4H). $^{13}$CNMR: 158.05, 156.85, 156.76, 156.58, 154.65, 153.87, 153.57, 151.52, 147.37, 145.18, 130.73, 128.37, 127.94, 125.55, 125.28, 117.76, 115.40, 115.16, 114.61, 111.00, 74.93, 72.72, 71.63, 71.54, 69.84. MS (ESI+) m/z: found 472.15 [M+H]$^+$ Example 31

Synthesis of 3-(3-Fluoro-benzyloxy)-5-(7,8,10,11,13,14-hexahydro-6,9,12,15-tetraoxa-1,3-diaza-cyclododeca[b]naphthalen-4-ylamino)-benzonitrile Structural formula of 3-(3-Fluoro-benzyloxy)-5-(7,8,10,11,13,14-hexahydro-6,9,12,15-tetraoxa-1,3-diaza-cyclododeca[b]naphthalen-4-ylamino)-benzonitrile is as follows:

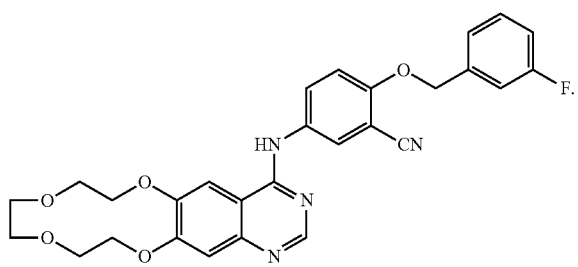 [SMILES: N#Cc1cc(Nc2ncnc3cc4c(cc23)OCCOCCOCCO4)ccc1OCc1cccc(F)c1]

Steps 31.1-31.7 were similar with the steps 1.1-1.7 in Example 1.

In the target compound of Example 31 represented by formula (I), n=1, R=CN; and ArCH$_2$XC$_6$H$_3$RN— is 3-(((3-FC$_6$H$_4$)CH$_2$O)C$_6$H$_3$CN)N—.

The synthesis method was similar to that of Example 30. The obtained product was a pale yellow solid with a melting point of 223-225° C. $^1$H NMR (400 MHz, DMSO-d6) δ 11.45 (s, 1H), 8.90 (s, 1H), 8.70 (s, 1H), 7.98 (d, J=2.6 Hz, 1H), 7.73 (dd, J=8.9, 2.6 Hz, 1H), 7.55 (d, J=6.1 Hz, 1H), 7.48 (s, 1H), 7.43-7.35 (m, 3H), 7.29-7.21 (m, 1H), 5.36 (s, 2H), 4.42 (s, 4H), 3.92-3.77 (m, 4H), 3.67 (s, 4H). $^{13}$CNMR: 158.24, 156.76, 156.35, 156.13, 154.75, 153.92, 153.80, 151.53, 147.29, 145.65, 131.24, 128.56, 127.82, 125.74, 125.42, 118.03, 116.12, 115.97, 114.71, 111.36, 73.16, 71.19, 70.97, 70.58, 69.18, 69.09, 68.93. MS (ESI+) m/z: found 516.18 [M+M]$^+$. Anal. calcd: C, 65.11; H, 4.88; F, 3.68; N, 10.85; O, 15.49.

Example 32

Synthesis of 4-(3-Fluoro-benzyloxy)-5-(2,5,8,11,14-pentaoxa-18,20-diaza-tricyclo[13.8.0.0$^{17,22}$]tricosa-16,18,20,22-tetraen-21-ylamino)-benzonitrile Structural formula of 4-(3-Fluoro-benzyloxy)-5-(2,5,8,11,14-pentaoxa-18,20-diaza-tricyclo[13.8.0.0$^{17,22}$]tricosa-16,18,20,22-tetraen-21-ylamino)-benzonitrile is as follows:

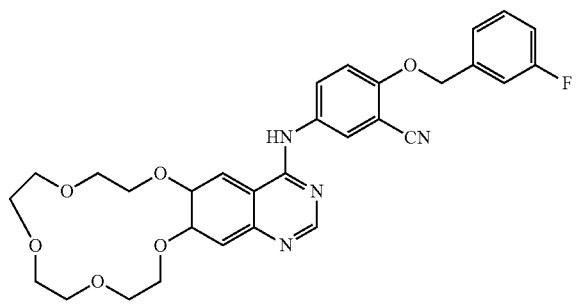 [SMILES: N#Cc1cc(Nc2ncnc3c2=CC2OCCOCCOCCOCCOC2C=3)ccc1OCc1cccc(F)c1]

Steps 32.1-32.7 were similar with the steps 1.1-1.7 in Example 1.

In the target compound of Example 32 represented by formula (I), n=2, R=CN; and ArCH$_2$XC$_6$H$_3$RN— is 3-(((3-FC$_6$H$_4$)CH$_2$O)C$_6$H$_3$CN)N—.

The synthesis method was similar to that of Example 30. The obtained product was a pale yellow solid with a melting point of 217-218° C. $^1$H NMR (400 MHz,) δ 11.04 (s, 1H), 8.69 (s, 1H), 8.28 (s, 1H), 7.89 (d, J=2.6 Hz, 1H), 7.65 (dd, J=8.9, 2.6 Hz, 1H), 7.44 (d, J=12.6, 7.1, 4.1 Hz, 1H), 7.24 (s, 4H), 7.17-7.11 (m, 1H), 5.24 (s, 2H), 4.28-4.15 (m, 4H), 3.84-3.78 (m, 4H), 3.60 (s, 8H). $^{13}$CNMR: 157.17, 156.52, 156.24, 156.03, 154.77, 154.01, 153.59, 151.46, 146.90, 145.25, 130.84, 128.12, 127.98, 125.29, 125.06, 117.96, 115.72, 115.43, 114.61, 111.28, 70.85, 70.37, 69.55, 69.37, 68.42, 68.56, 68.47, 68.38, 68.17. MS (ESI+) m/z: found 562.22 [M+H]$^+$.

BIOLOGICAL EXAMPLES

Example 33

In vitro anticancer activity of 35 target compounds was tested by MTT assay.

Cell lines to be tested: human hepatoma cell line (HepG2), human lung cancer cell line (A549), human prostate cancer cell line (DU145), human breast cancer cell line (MCF-7), human neuroblastoma cell line (SH-SY5Y), human gastric mucosal cell line (Ges-1) and human embryonic lung fibroblast cell line (CCC-HPF-1) (the cells to be tested were purchased from the Cancer Hospital of Chinese Academy of Medical Sciences).

The cells in logarithmic growth phase were treated to prepare a single cell suspension, with the cell density adjusted, which was seeded in a 96-well cell culture plate. About 2×10³ cells were contained in 100 μL per well, and cultured in a cell incubator at 37° C., 5% $CO_2$, and saturated humidity for 24 h. The used medium was aspirated and abandoned, and then 100 μL of the target compound in different concentrations (0.1 μM-100 μM) were added for drug treatment. Five duplicate wells were prepared for each concentration. The background blank well, negative control well and positive control well were also prepared. All the wells were placed in a cell culture incubator at 37° C., 5% $CO_2$, saturated humidity for another 72 h. Then, each well was added with 10 μL of MTT solution (5 mg/mL) and incubated for another 4 h. After that, each well was added with 100 μL of 10% SDS-0.1% $NH_4Cl$ (10% SDS purchased from Beijing Mengyimei Biotechnology Co., Ltd.) solution, and incubated at 37° C. for 10 h in the dark. Then, the absorbance OD was measured at 570 nm using a microplate reader at a reference wavelength of 650 nm. Cell proliferation inhibition was calculated according to the following formula: % inhibition=$(OD_{control}-OD_{treat})(OD_{control}-OD_{blank})$×100. $IC_{50}$ value, i.e., 50% proliferation inhibition concentration, was calculated by SPSS 16.0 software. Each group was performed at least three times in parallel.

The inhibitory activities of 35 target compounds against tumor cell strains HepG2, A549, MCF-7, DU145 and SH-SY5Y were tested by MTT assay (Table 1). Some compounds with optimal antitumor activity were selected. Among them, compounds 3, 5 and 13 have strong specific inhibitory activity on A549; compound 17 has a strong specific inhibitory effect on MCF-7; compound 23 has a strong specific inhibitory effect on DU145; compound 11 has a strong specific inhibitory effect on SH—SY5Y; compounds 29, 31, 34, and 35 have a good inhibitory effect on proliferation of at least three of the five tumor cells; especially, compound 35 has high anticancer activity on all the five tumor cells.

Experiment of Compound 35 Against Hepatocellular Carcinoma HepG2 In Vivo

Biological evaluation of exemplary compound 35 shown in formula (I) of the present invention (the serial number is shown in Table 1) and its combination with regorafenib or sorafenib in the treatment of nude mice bearing HepG2 cancer Compound 35 is N-(4-((4-trifluoromethylphenyl)methoxy) phenyl)-6,7-(benzo-15-crown-5)-4-quinazolinamine.

Its structural formula is as follows:

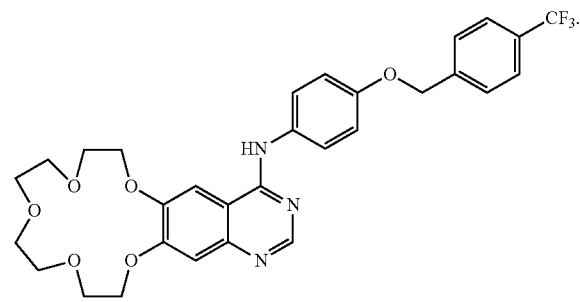 [SMILES: FC(F)(F)c1ccc(COc2ccc(Nc3ncnc4cc5c(cc34)OCCOCCOCCOCCO5)cc2)cc1]

FIGS. 5, 6, 7, 8, 9, and 10 show the biological activity of exemplary compound 35 shown in formula (I) of the present invention in the treatment of nude mice bearing HepG2 cancer cells.

Figure 5:
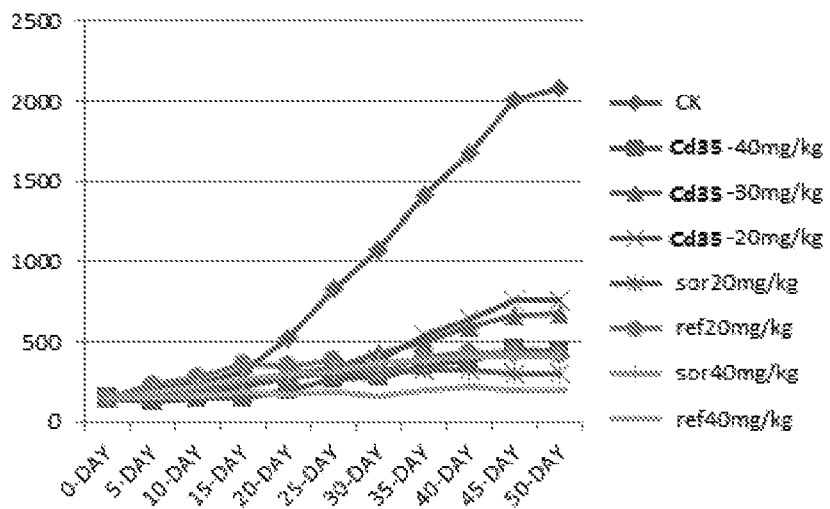
FIG. 5 shows the changes in tumor volume of nude mice bearing HepG2 cancer cells treated with compound 35, sorafenib and regorafenib, respectively.

FIG. 5 illustrates that compound 35, sorafenib and regorafenib can slow down the tumor growth with increasing drug dose during the treatment of nude mice bearing HepG2 cancer cells, but none of them can inhibit the tumor growing. The best therapeutic effect is to make the tumor stop growing; and even the best-effect drug regorafenib plays little role in reducing tumor size.

Figure 6:
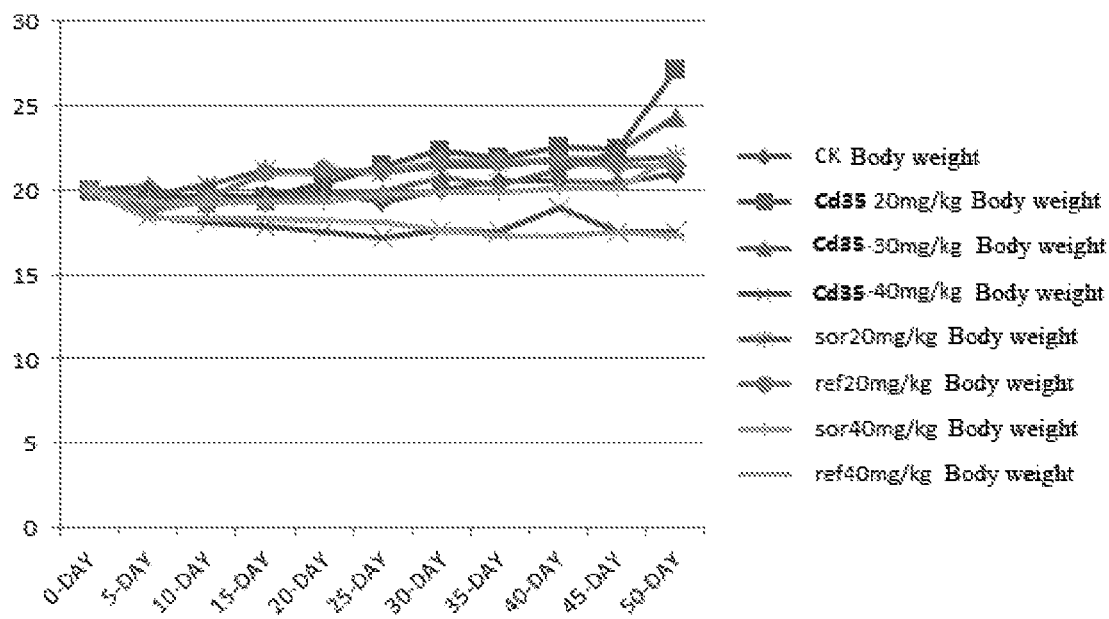
FIG. 6 shows the changes in body weight of nude mice during the treatment of liver cancer with compound 35, sorafenib and regorafenib.

As shown in FIG. 6, when the dosages of compound 35 and regorafenib are 40 mg/Kg, the weight loss of nude mice is similar, indicating that the toxicity thereof is roughly equivalent. When the dosage of sorafenib is 40 mg/Kg, the weight loss of nude mice is relatively slow, indicating that the toxicity is the lowest. However, when the dosage is 20 mg/Kg, the body weight of the mice treated with compound 35 is significantly increased, and is much higher than that of the group of blank and the groups treated with regorafenib and sorafenib, indicating that the toxicity of compound 35 of the present invention is lower than that of regorafenib and sorafenib.

Figure 7:
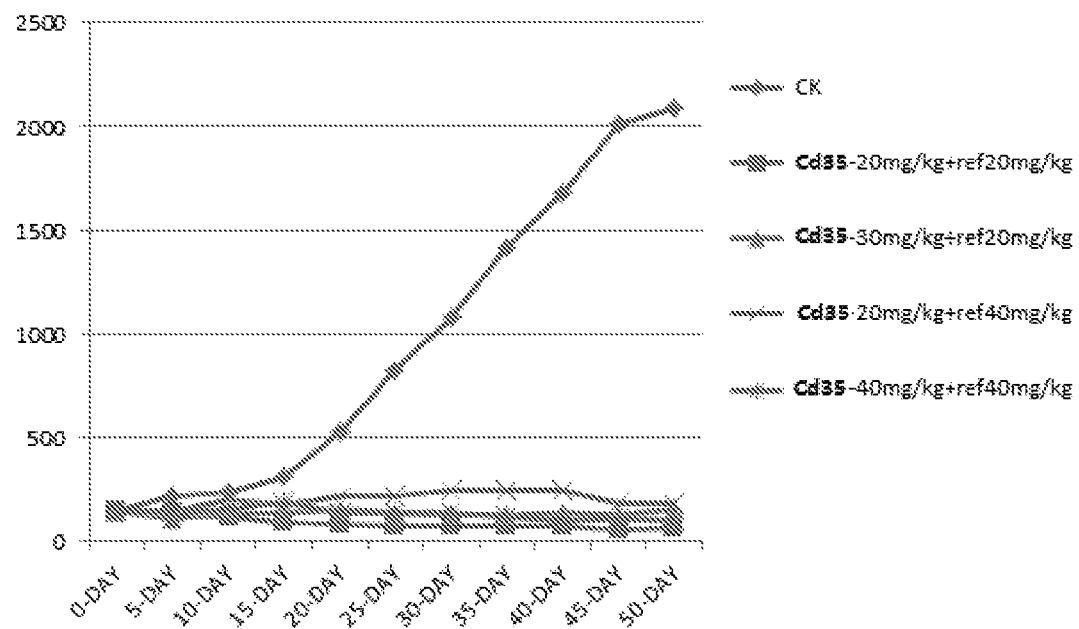
FIG. 7 shows the change in tumor volume of nude mice bearing HepG2 cancer cells treated with compound 35 in combination with regorafenib.

FIG. 7 shows that the therapeutic effect of compound 35 combined with regorafenib on HepG2 is significantly better at four different doses. The tumor volume is significantly reduced in nude mice bearing HepG2 cancer cells at four different doses. When the dose of each drug in the combination of compound 35 with regorafenib is 20 mg/Kg, the tumor volume is significantly reduced, and the mice are nearly cured (in fact, two of the five mice are cured on day 60, and the tumors of the other three are also very small). This therapeutic effect is far better than the therapeutic effect of regorafenib alone. The most important thing is that the condition of the nude mice in this case is far better than that treated with regorafenib alone at 40 mg/Kg, which indicates that the therapeutic effect of compound 35 combined with regorafenib is far better than that of regorafenib alone.

Figure 8:
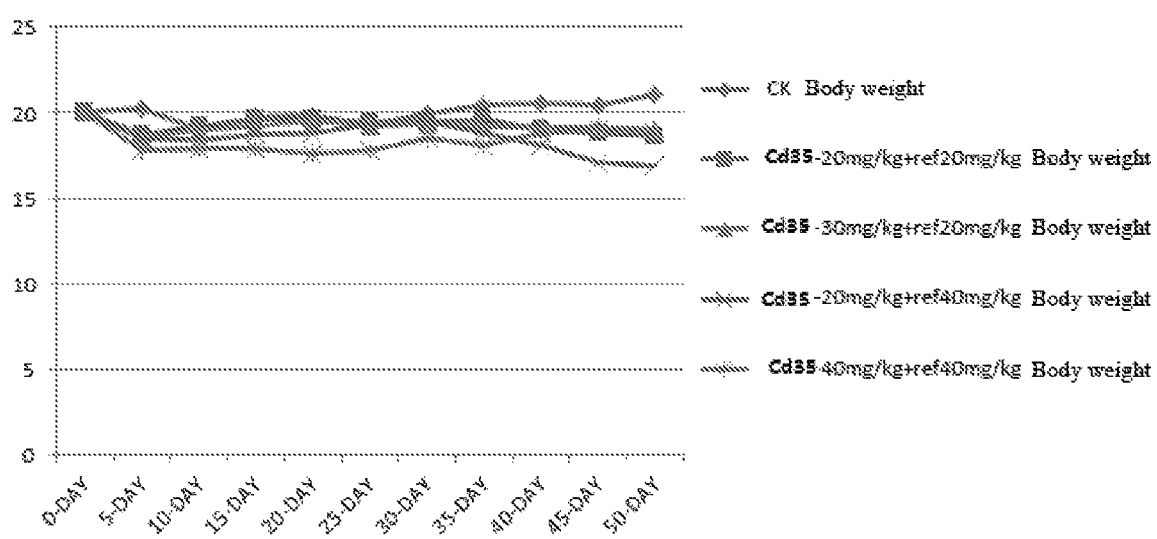
FIG. 8 shows the change in body weight of nude mice bearing HepG2 cancer cells treated with compound 35 in combination with regorafenib.

FIG. 8 shows that the weight loss of nude mice bearing HepG2 cancer cells is relatively slow in the treatment with compound 35 combined with regorafenib at four different doses, which is not much different from that of blank nude mice. This shows that the therapeutic effect is improved, and the toxicity is not increased.

Figure 9:
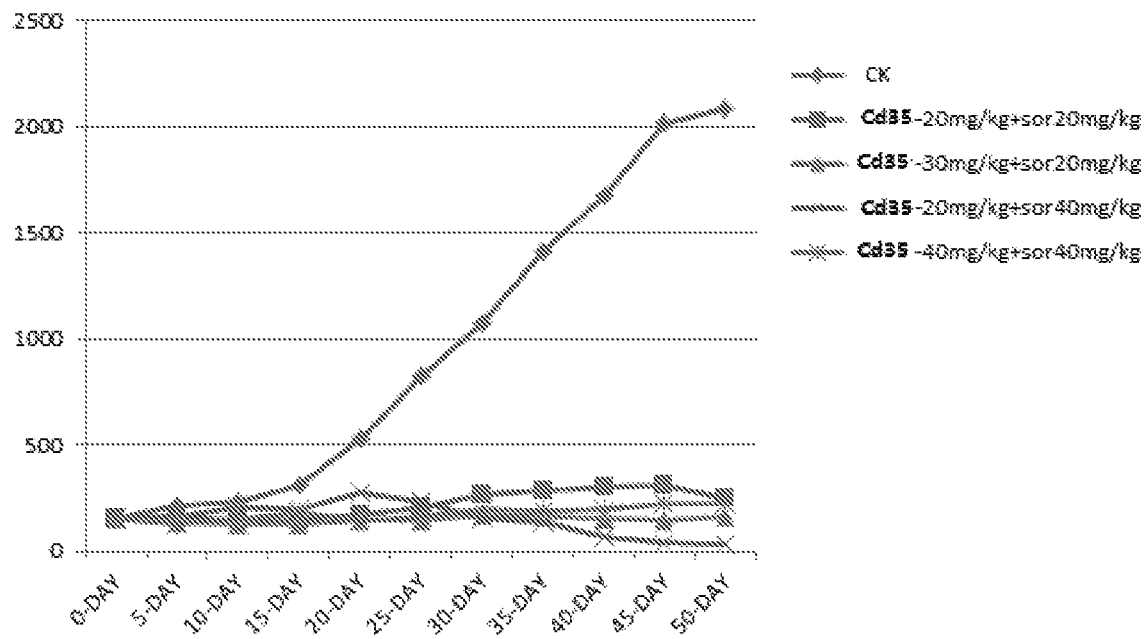
FIG. 9 shows the change in tumor volume of nude mice bearing HepG2 cancer cells treated with compound 35 in combination with sorafenib.

FIG. 9 shows the therapeutic effect of compound 35 combined with sorafenib on HepG2 at four different doses. The compound 35 at a dose of 20 mg/Kg combined with sorafenib at a dose of 40 mg/Kg gives the best therapeutic effect and the tumor is almost cured on day 50. When compound 35 and sorafenib are used at 30 mg and 20 mg respectively, the tumor volume is also decreased.

Figure 10:
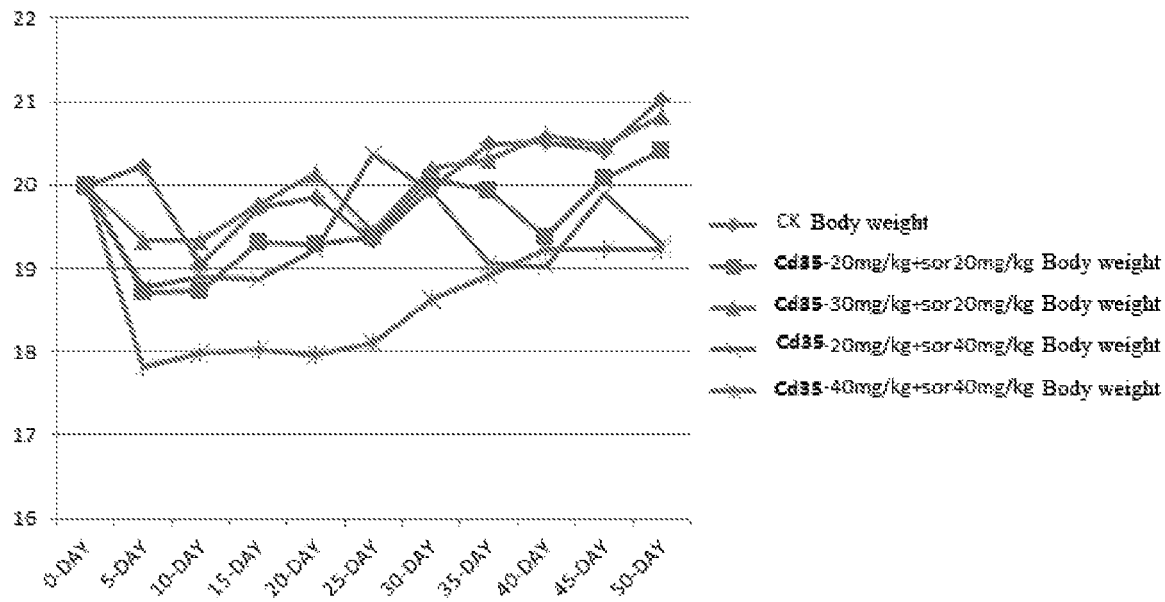
FIG. 10 shows the change in body weight of nude mice bearing HepG2 cancer cells treated with compound 35 in combination with sorafenib.

FIG. 10 shows the change in body weight of nude mice treated with compound 35 in combination with sorafenib. When the dosages of compound 35 and Sorafenib are (20 mg+20 mg) and (30 mg+20 mg), the weights of nude mice are close to that of blank nude mice, and their weights are increasing, indicating the low toxicity of this ratio. The toxicity for the dose of 20 mg+40 mg is similar to that of sorafenib alone. The effect of these drug combinations is better than that of the drugs alone. The weight loss is not significant, and the toxicity is accordingly reduced.

The compound numbers shown in Table 1 below correspond to the following compounds:
N-(2-((4-nitrophenyl)methoxy)phenyl)-6,7-(benzo-9-crown-3)-4-quinazolinamine (1), N-(3-((4-nitrophenyl)methoxy)phenyl)-6,7-(benzo-9-crown-3)-4-quinazolinamine (2), N-(4-((4-nitrophenyl)methoxy)phenyl)-6,7-(benzo-9-crown-3)-4-quinazolinamine (3), N-(2-((p-fluorophenyl)methoxy)phenyl)-6,7-(benzo-9-crown-3)-4-quinazolinamine (4), N-(3-((p-fluorophenyl)methoxy)phenyl)-6,7-(benzo-9-crown-3)-4-quinazolinamine (5), N-(4-((p-fluorophenyl)methoxy)phenyl)-6,7-(benzo-9-crown-3)-4-quinazolinamine (6), N-(2-((4-trifluoromethylphenyl)methoxy) phenyl)-6,7-(benzo-9-crown-3)-4-quinazolinamine (7), N-(3-((4-trifluoromethylphenyl)methoxy) phenyl)-6,7-(benzo-9-crown-3)-4-quinazolinamine (8), N-(4-((4-trifluoromethylphenyl)methoxy) phenyl)-6,7-(benzo-9-crown-3)-4-quinazolinamine (9), N-(3-((4-cyanophenyl)methoxy) phenyl)-6,7-(benzo-12-crown-4)-4-quinazolinamine (10), N-(4-((4-cyanophenyl)methoxy) phenyl)-6,7-(benzo-12-crown-4)-4-quinazolinamine (11), N-(2-((4-pyridyl)methoxy)phenyl)-6,7-(benzo-9-crown-3)-4-quinazolinamine (12), N-(2-((3-chloro,4-fluorophenyl) methoxy) phenyl)-6,7-(benzo-9-crown-3)-4-quinazolinamine (13), N-(3-((3-chloro,4-fluorophenyl)methoxy) phenyl)-6,7-(benzo-9-crown-3)-4-quinazolinamine (14), N-(4-((3-chloro,4-fluorophenyl)methoxy) phenyl)-6,7-(benzo-9-crown-3)-4-quinazolinamine (15), N-(3-((p-fluorophenyl)methoxy) phenyl)-6,7-(benzo-12-crown-4)-4-quinazolinamine (16), N-(4-((p-fluorophenyl)methoxy) phenyl)-6,7-(benzo-12-crown-4)-4-quinazolinamine (17), N-(2-((4-nitrophenyl)methoxy) phenyl)-6,7-(benzo-12-crown-4)-4-quinazolinamine (18), N-(3-((4-nitrophenyl) methoxy) phenyl)-6,7-(benzo-12-crown-4)-4-quinazolinamine (19), N-(4-((4-nitrophenyl)methoxy) phenyl)-6,7-(benzo-12-crown-4)-4-quinazolinamine (20), N-(3-((phenyl)methoxy)phenyl)-6,7-(benzo-12-crown-4)-4-quinazolinamine (21), N-(2-((4-trifluoromethylphenyl) methoxy) phenyl)-6,7-(benzo-12-crown-4)-4-quinazolinamine (22), N-(3-((4-trifluoromethylphenyl) methoxy) phenyl)-6,7-(benzo-12-crown-4)-4-quinazolinamine (23), N-(4-((4-trifluoromethylphenyl) methoxy) phenyl)-6,7-(benzo-12-crown-4)-4-quinazolinamine (24), N-(3-((p-fluorophenyl)methoxy) phenyl)-6,7-(benzo-15-crown-5)-4-quinazolinamine (25), N-(4-((p-fluorophenyl)methoxy) phenyl)-6,7-(benzo-15-crown-5)-4-quinazolinamine (26), N-(2-((phenyl)methoxy) phenyl)-6,7-(benzo-15-crown-5)-4-quinazolinamine (27), N-(3-((phenyl)methoxy)phenyl)-6,7-(benzo-15-crown-5)-4-quinazolinamine (28), N-(4-((phenyl)methoxy)phenyl)-6,7-(benzo-15-crown-5)-4-quinazolinamine (29), N-(2-((4-nitrophenyl)methoxy) phenyl)-6,7-(benzo-15-crown-5)-4-quinazolinamine (30), N-(3-((4-nitrophenyl)methoxy) phenyl)-6,7-(benzo-15-crown-5)-4-quinazolinamine (31), N-(4-((4-nitrophenyl)methoxy) phenyl)-6,7-(benzo-15-crown-5)-4-quinazolinamine (32), N-(2-((4-trifluoromethylphenyl)methoxy) phenyl)-6,7-(benzo-15-crown-5)-4-quinazolinamine (33), N-(3-((4-trifluoromethylphenyl) methoxy) phenyl)-6,7-(benzo-15-crown-5)-4-quinazolinamine (34), N-(4-((4-trifluoromethylphenyl) methoxy) phenyl)-6,7-(benzo-15-crown-5)-4-quinazolinamine (35), 2-(3-Fluoro-benzyloxy)-5-(7,8,10, 11-tetrahydro-6,9,12-tri oxa-1,3-diaza-cyclonona[b] naphthalen-4-ylamino)-benzonitrile (36), 3-(3-Fluoro-benzyloxy)-5-(7,8,10,11,13,14-hexahydro-6,9,12,15-tetraoxa-1,3-diaza-cyclododeca[b]naphthalen-4-ylamino)-benzonitrile (37), 4-(3-Fluoro-benzyloxy)-5-(2,5,8,11,14-pentaoxa-18,20-diaza-tricyclo[13.8.0.0$^{17,22}$]tricosa-16,18, 20,22-tetraen-21-ylamino)-benzonitrile (38), and Gefitinib. Their IC$_{50}$ values for five common cells are also shown in Table 1.

TABLE 1

Test results of tumor cell proliferation inhibition activity for some exemplary compounds of formula (I) of the present invention and the positive drug

| Compounds | Tumor inhibition rate (IC$_{50}$, μM) | | | | |
|---|---|---|---|---|---|
| | HepG2 | SH-SY5Y | A549 | MCF-7 | DU145 |
| 1 | 50.158 | >100 | 28.424 | >100 | 85.647 |
| 2 | 65.330 | 36.587 | 15.471 | 42.419 | >100 |
| 3 | >100 | 55.183 | 6.619 | 39.684 | >100 |
| 4 | >100 | 84.522 | 14.354 | >100 | >100 |
| 5 | >100 | 55.320 | 7.843 | 78.235 | >100 |
| 6 | >100 | 82.683 | 43.256 | 65.217 | >100 |
| 7 | 87.433 | >100 | >100 | >100 | >100 |
| 8 | >100 | 19.273 | >100 | >100 | >100 |
| 9 | >100 | 30.422 | >100 | >100 | >100 |
| 10 | >100 | >100 | >100 | >100 | >100 |
| 11 | 67.384 | 9.886 | 81.339 | >100 | >100 |
| 12 | 31.256 | >100 | >100 | >100 | >100 |
| 13 | >100 | >100 | 9.429 | >100 | 88.612 |
| 14 | 43.582 | 22.663 | >100 | >100 | 90.065 |
| 15 | 76.540 | >100 | >100 | >100 | >100 |
| 16 | >100 | 22.835 | >100 | >100 | >100 |
| 17 | >100 | 20.669 | >100 | 8.306 | >100 |
| 18 | 60.765 | 75.493 | 29.86 | >100 | >100 |
| 19 | >100 | >100 | >100 | >100 | >100 |
| 20 | 19.396 | 58.633 | >100 | 66.505 | >100 |
| 21 | >100 | 22.835 | >100 | >100 | >100 |
| 22 | >100 | >100 | >100 | >100 | >100 |
| 23 | 33.956 | 20.026 | 24.893 | 17.625 | 2.756 |
| 24 | >100 | >100 | >100 | >100 | >100 |
| 25 | 19.023 | 20.036 | >100 | >100 | >100 |
| 26 | 55.468 | 39.282 | 43.949 | >100 | >100 |
| 27 | 29.244 | 24.000 | 48.531 | >100 | >100 |
| 28 | 55.468 | 39.282 | 43.949 | >100 | >100 |
| 29 | 11.863 | 5.254 | 29.454 | 11.965 | 8.798 |
| 30 | 48.055 | >100 | >100 | >100 | >100 |
| 31 | 9.817 | 8.416 | 19.785 | 6.410 | 13.846 |
| 32 | >100 | >100 | >100 | >100 | >100 |
| 33 | >100 | >100 | 30.662 | 28.468 | >100 |
| 34 | 5.696 | 8.561 | 8.516 | 8.478 | 26.87 |
| 35 | 3.336 | 2.138 | 8.564 | 10.025 | 8.803 |
| 36 | >100 | >100 | 3.518 | >100 | 0.310 |
| 37 | 19.568 | >100 | 0.455 | >100 | >100 |
| 38 | 2.770 | 1.287 | 14.464 | 2.797 | 0.803 |
| Gefitinib | 29.790 | 18.216 | 14.803 | >100 | >100 |

Example 34

Effect of compound 3 of Formula (I) of the present invention (as listed in Table 1) on cell cycle Experiment procedure: A549 cells in logarithmic growth phase (purchased from the Cancer Hospital of Chinese Academy of Medical Sciences) were seeded into 6-well cell culture plates, adjusted to 5×10$^5$ cells per well, and cultured in an incubator at 37° C., 5% CO$_2$, and saturated humidity for 24 h. The used medium was discarded. The cells were treated with the target compounds in different concentrations for 48 h, and grouped to an administration group and a control group (non-administered). The cells were digested with 0.25% trypsin to form a single cell suspension, centrifuged at 1500 r/min for 5 min. The supernatant was discarded, and the cells were collected. The cells were washed twice with precooled PBS buffer, centrifuged at 1500 r/min for 5 min, added to 5 mL of precooled 70% ethanol, and placed at 4° C. for at least 24 h. After centrifugation, the supernatant was discarded, and the cells were washed twice with PBS and collected by centrifugation. The cells were suspended in 400 μL PBS, added with 30 μL of RNaseA (purchased from Corning Inc., USA) at the concentrations from 1 mg/mL to 50 μg/mL, and incubated at 37° C. for 30 min. The centrifuge tube was then inserted into an ice bath to stop digestion. After the tube was cooled, 50 μL of PI staining solution (500 μg/mL) (purchased from Corning Inc., USA) was added to a final concentration of 50 μg/mL. The tube was immersed in an ice bath to perform straining in the dark for 30 min-40 min, filtered through a 300 mesh nylon mesh, and tested by flow cytometer (FACS Vantage SE: BD, USA).

Compound 3: N-(4-((4-nitrophenyl) methoxy) phenyl)-6,7-(benzo-9-crown-3)-4-quinazolinamine

TABLE 2

Effect of compound 3 of Formula (I) of the present invention on A549 cell cycle

| Groups | Cell proportion, % | | |
|---|---|---|---|
| (μM) | $G_0/G_1$ | $G_2/M$ | S |
| 0 | 83.71 ± 0.21 [a] | 4.03 ± 0.10 [a] | 12.25 ± 0.11 |
| 5 | 84.51 ± 0.32 [a] | 3.06 ± 0.12 | 12.42 ± 0.10 |
| 10 | 85.58 ± 0.44 [a] | 3.05 ± 0.19 | 11.39 ± 0.64 |
| 20 | 87.23 ± 0.31 [a] | 1.41 ± 0.05 [a] | 11.68 ± 0.26 |
| 40 | 90.08 ± 0.62 [a] | 2.04 ± 0.14 [a] | 7.90 ± 0.50 [a] |

Note:
[a] indicates a comparison between experiment groups, $P < 0.05$.

The present invention investigated compound 3 (as listed in Table 1) by cell cycle experiments. The cell cycle results indicate that the percentages of cells in $G_0/G_1$ phase increases gradually as the drug concentration increased. The percentage of cells in $G_0/G_1$ phase increases from 83.71% to 90.08% as the concentration increases from 0 μM to 40 μM, and the difference between the groups is significant ($P<0.05$). That is, compound 3 can block A549 in $G_0/G_1$ phase.

It can be seen that compounds of formula (I) provided by the present invention can kill tumor cells in $G_0/G_1$ phase, indicating that the target compounds of formula (I) provided by the present invention belongs to a targeted medicine.

Example 35

Biological evaluation of exemplary compound 3 of formula (I) of the present invention on nude mice bearing A549 cancer cells Compound 3: N-(4-((4-nitrophenyl)methoxy) phenyl)-6,7-(benzo-9-crown-3)-4-quinazolinamine Structural formula of N-(4-((4-nitrophenyl)methoxy) phenyl)-6,7-(benzo-9-crown-3)-4-quinazolinamine is as follows:

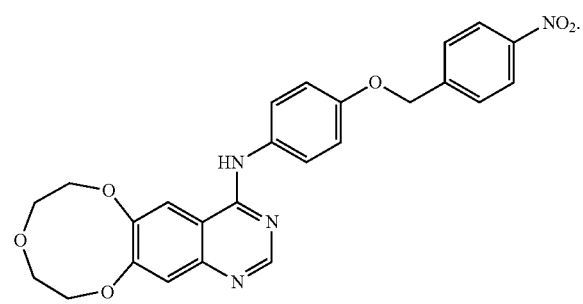 [SMILES: O=[N+]([O-])c1ccc(COc2ccc(Nc3ncnc4cc5c(cc34)OCCOCCO5)cc2)cc1]

The results in FIG. 1 show that exemplary compound 3 of formula (I) of the present invention has a remarkable tumor inhibitory effect on nude mice bearing A549 cancer cells. When administered at the same dose (i.e., 45 mg/Kg), its inhibitory activity against A549 cancer cells was significantly higher than the epoch-making targeted medicine gefitinib (also known as Iressa, a positive control drug). Tumor was significant inhibited at concentrations up to 60 mg/Kg, and grew little or limitedly. In blank control group, tumor grew rapidly. FIG. 1 indicates that compound 3 has the potential to become a new drug in inhibiting the activity of A549 tumor, which is worthy of vigorous research and development.

Figure 2:
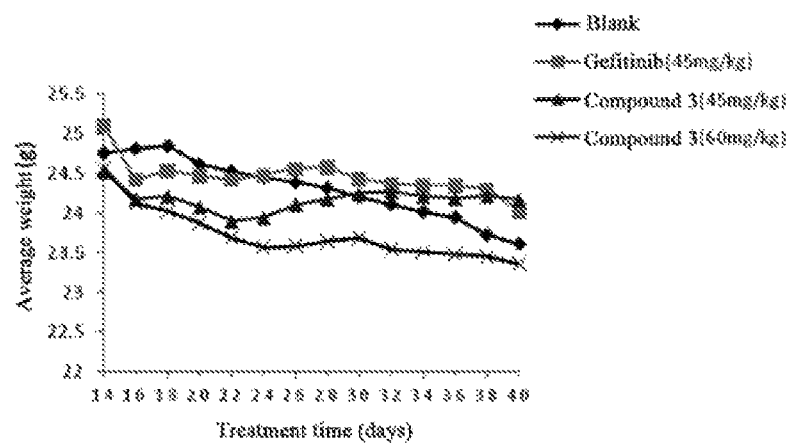
FIG. 2 shows the test results of body weights of nude mice bearing tumor (A549) treated with compound 3 in examples of the present invention and a positive control drug (a graph of body weights of nude mice with respect to the number of experiment days).

FIG. 2 illustrates that compound 3 is less toxic. The body weight of nude mice bearing A549 cancer cells administrated with compound 3 was roughly equivalent to that of the nude mice administrated with gefitinib, and the administration dose was also comparable. Compound 3 was more toxic than gefitinib at the beginning of the administration. With further administration, the effect of compound 3 on body weight of nude mice was significantly reduced, and the weight of nude mice was increased. Especially in the later stages of administration, the weight of the nude mice administrated with compound 3 was increased and even exceeded that of the gefitinib group. This is very rare and advantageous, because the impact of the administration on the host or the nude mouse itself will directly determine whether the development would be successful or not. The body weights were increased for both target compound 3 and gefitinib groups compared to the blank control during the treatment, and compound 3 was more advantageous than gefitinib as treatment time prolonged. It is especially important that the body weight was not decreased significantly when the concentration was increased to 60 mg/Kg. On the contrary, the body weight decrease was slowed down in the late stage of the treatment, and the body weight was almost equivalent to that of the blank control group. It was demonstrated that the drug has no significant toxicity at increased doses and it provides an important basis for the treatment with increased dose.

Both FIGS. 1 and 2 above show that compound 3 is highly active and less toxic in the treatment of nude mice bearing A549 cancer cells. In particular, the ability to inhibit tumor growth was significantly increased when the concentration of compound 3 was increased to 60 mg/Kg, while the body weight did not decrease significantly. In the later stage, the body weight was almost equivalent to that of the blank mice, indicating that the drug at an increased dose was not significantly toxic, provided an important basis for the treatment with increased dose, and showed a very good development prospects.

Example 36

Biological evaluation of exemplary compound 23 (as listed in Table 1) of formula (I) of the present invention on nude mice bearing DU145 cancer cells Compound 23: N-(3-((4-trifluoromethylphenyl) methoxy) phenyl)-6,7-(benzo-12-crown-4)-4-quinazolinamine Structural formula of N-(3-((4-trifluoromethylphenyl) methoxy) phenyl)-6,7-(benzo-12-crown-4)-4-quinazolinamine is as follows:

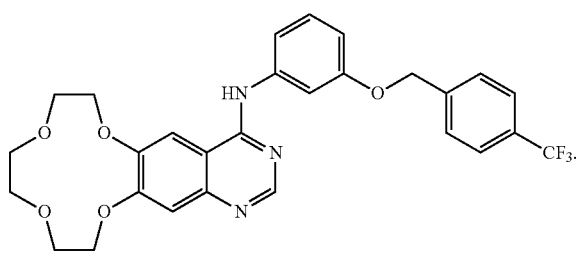 [SMILES: FC(F)(F)c1ccc(COc2cccc(Nc3ncnc4cc5c(cc34)OCCOCCOCCO5)c2)cc1]

Figure 3:
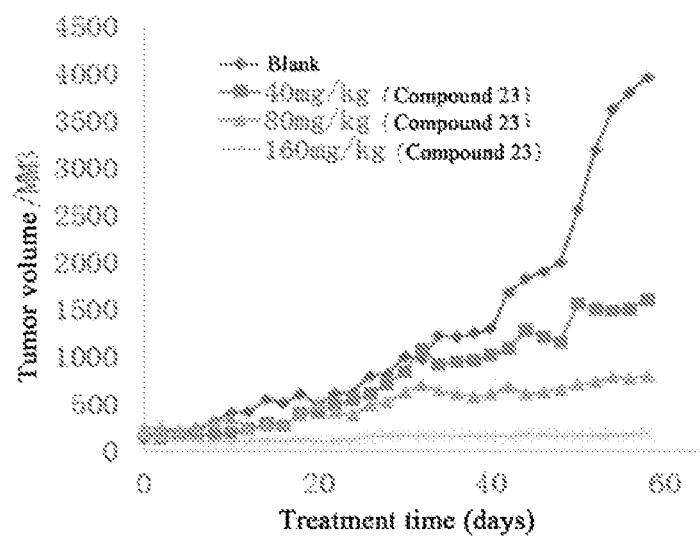
FIG. 3 shows the test results of inhibitory activity of compound 23 in examples of the present invention and a blank control in nude mice bearing tumor (DU145) (a graph of the volumes of the treated tumor with respect to the number of experiment days).
Figure 4:
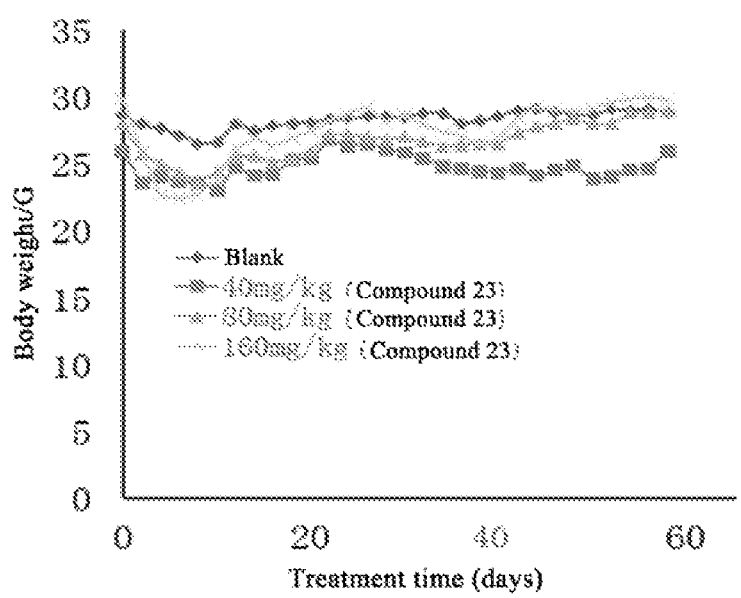
FIG. 4 shows the test results of the body weights of the nude mice bearing tumor (DU145) treated with compound 23 in examples of the present invention and a blank control (a graph of body weights of nude mice with respect to the number of experiment days).

FIGS. 3 and 4 illustrates the experiment results for the nude mice bearing tumor (DU145) treated with compound 23 of formula (I) of the present invention.

FIG. 3 shows that compound 23 has a significant antitumor effect on nude mice bearing DU145 cancer cells. Compound 23 administered at three different doses was able to inhibit the growth of DU145 cancer cells significantly. Especially after 50 days of treatment, the tumor in the blank control group was increased significantly, while the tumors treated with the target compound 23 at three different doses were inhibited well. When the dose was 80 mg/Kg and 160 mg/Kg, respectively, the tumors were no longer grown almost. Especially when the dose was 160 mg/Kg, the tumors were completely inhibited, almost without changes, and no drug resistance was shown. When the dose was 80 mg/Kg, the tumors were increased somewhat at the beginning, but in the later stage, the tumors were also stopped growing for a long time. The inhibitory effect of compound 23 was very significant when compared with the blank control. Therefore, the results of in vivo experiments demonstrate that compound 23 has the potential to develop a new prostate cancer drug for DU145.

FIG. 4 illustrates that the toxicity of compound 23 is very low. During the treatment, except for the first two days, the body weights of the nude mice bearing DU145 cancer cells were not decreased but increased. This trend became significantly as the treatment time increased. The weights of the nude mice were even heavier than that of the blank control group (e.g., the body weights after treating for 50 days at a dose of 80 mg/Kg). Especially, when the nude mice were administered at a high dose of 160 mg/kg, no significant toxicity was observed. This is rare in current developed drugs. This also proves from another aspect that compound 23 among the compounds of formula (I) developed has low potential toxicity and high targeting. At present, the major defect of all clinical drugs for treating cancer is their high toxicity. Significant weight loss during treatment causes host to become thinner and die. Compound 23 of the present invention can significantly increase the body weight of the nude mice after 4 days of treatment, which is of great significance for supporting the successful development of compound 23 into a novel prostate cancer therapeutic drug.

Combining the experiment results of FIGS. 3 and 4 above, it is shown that compound 23 has the potential to be successfully developed into an important targeted medicine for treating prostate cancer. The compound has highly activity, little toxicity and good resistance to drug resistance during the treatment of DU145 cancer cells in nude mice. In the past, the development of important targeted medicines for treating prostate cancer failed due to toxicity to the host and drug resistance. In vivo experiments for compound 23 have demonstrated risks in both aspects above decrease significantly. Therefore it is possible to develop targeted medicines for treating prostate cancer.

The above is only the preferred embodiment of the present invention, and is not intended to limit the present invention. Any modifications, equivalent substitutions, and improvements, etc., made within the spirit and principle of the invention are intended to be included within the scope of the invention.

The invention claimed is:

1. A compound of anilino polyethylene glycol ether cycloquinazoline substituted with a substituted arylmethyl heteroatomic group represented by formula (I), or a pharmaceutically acceptable salt, ester or solvate thereof,

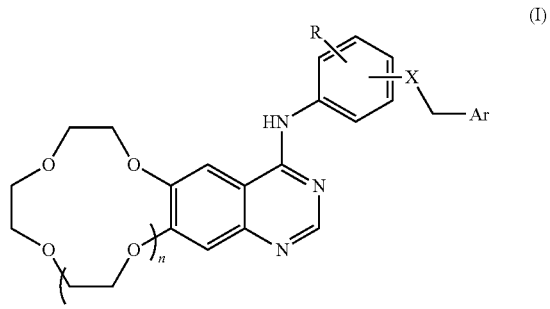

wherein, n is 0, 1, 2, 3, 4, 5 or 6; X represents —O—, —S—, —NH—, —SO—, —SO$_2$— or —CO—; R represents H—, F—, Cl—, Br—, I—, —CN, —CH$_3$, —CF$_3$ or —CCl$_3$;

Ar represents a monosubstituted, disubstituted or unsubstituted benzene, naphthalene, pyridine, furan, thiophene, indole, pyrimidine, benzopyrimidine, imidazole, thiazole, oxazole, benzoxazole or benzothiazole;

when Ar is monosubstituted, a monosubstituent R$_1$ group on Ar represents —NO$_2$, —CF$_3$, —Cl$_3$, —CBr$_3$, —CH$_2$CF$_3$, —H, F—, Cl—, Br—, —CH$_3$, —CH$_2$CHCH$_2$, —CN, —CHO, —COOH, —COOCH$_3$, —COOCH$_2$CH$_3$, —CONH$_2$, —CON(CH$_3$)$_2$, —N(CH$_3$)$_2$, —N(CH$_2$CH$_3$)$_2$, —OCH$_3$ or —OCH$_2$CH$_3$; and when Ar is disubstituted, disubstituents R$_2$ and R$_3$ on Ar each independently represent F—, Cl—, Br—, —CH$_3$, CH$_3$O—, —CF$_3$, —CN, —CHO, —COOH, —COOCH$_3$, —COOCH$_2$CH$_3$, —CONH$_2$, —CON(CH$_3$)$_2$, —OCH$_3$, —N(CH$_3$)$_2$ or —N(CH$_2$CH$_3$)$_2$.

2. The compound of formula (I), or the pharmaceutically acceptable salt, ester or solvate thereof according to claim 1, wherein n is 0, 1, 2 or 3, X represents —O—, —S— or —NH—; R represents H—, F—, Cl— or —CF$_3$; and Ar is

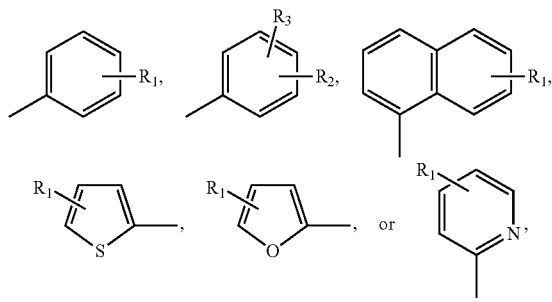

wherein R$_1$ represents —NO$_2$, —CF$_3$, —CCl$_3$, H—, Cl—, F—, —CH$_3$, —CN, —CHO, —COOH, —COOCH$_3$, —N(CH₃)₂ or —OCH₃; and R₂ and R₃ independently represent —F, —Cl, —CH₃, CH₃O—, —CF₃, —CN, —CHO, —COOH or —N(CH₃)₂.

3. The compound of formula (I), or the pharmaceutically acceptable salt, ester or solvate thereof according to claim 1, wherein the pharmaceutically acceptable salt comprises:
   (1) a salt formed with an inorganic acid or inorganic base;
   (2) a salt formed with an organic acid or organic base; and
   (3) a pharmaceutically acceptable cation.

4. A pharmaceutical composition comprising the compound of formula (I), or the pharmaceutically acceptable salt, ester or solvate thereof according to claim 1.

5. The pharmaceutical composition according to claim 4, wherein the pharmaceutical composition is formulated as a solid or liquid oral preparation, or an injection.

6. A method for preparing the compound of formula (I), or the pharmaceutically acceptable salt, ester or solvate thereof according to claim 1, comprising:
   (1) reacting a compound of formula (II) with a compound of formula (III) to obtain a compound of formula (IV), and reacting the compound of formula (IV) with Y—CH₂Ar in an organic solvent to obtain the compound of formula (I);

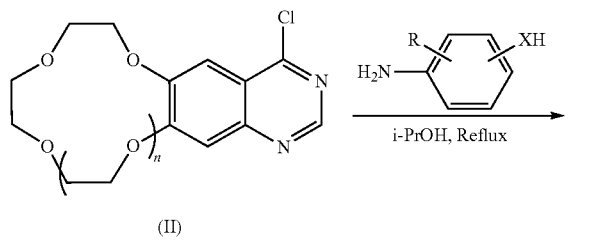

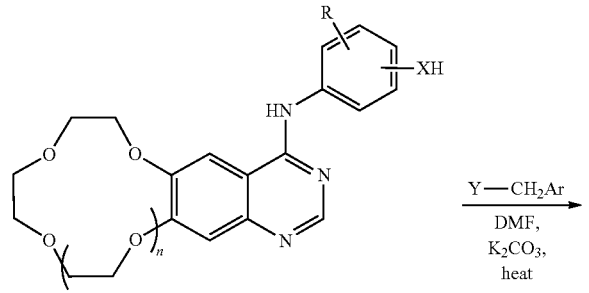

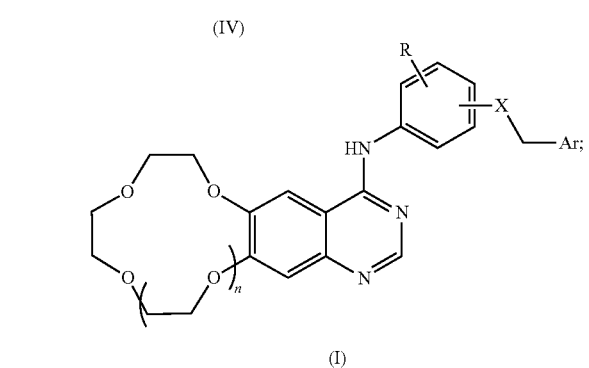

or
   (2) reacting a compound of formula (III) with Y—CH₂Ar to obtain a compound of formula (V), and reacting the compound of formula (V) with a compound of formula (II) to obtain the compound of formula (I);

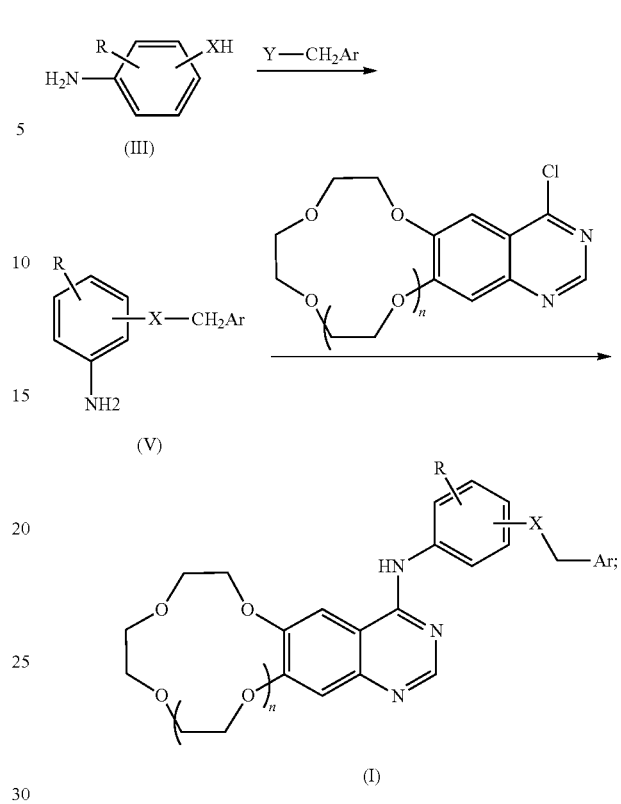

Y represents F, Cl, Br, I or a sulfonate group.

7. A method of treating a tumor in a subject comprising administering a therapeutically effective amount of an antitumor therapeutic drug comprising the compound of formula (I), or the pharmaceutically acceptable salt, ester or solvate thereof, or a pharmaceutical composition comprising the compound of formula (I), or the pharmaceutically acceptable salt, ester or solvate thereof according to claim 1 to a subject in need thereof, wherein
   the tumor is lung cancer, prostate cancer, liver cancer, stomach cancer, neuroblastoma, breast cancer, gynecologic cancer, esophageal cancer, or colon cancer.

8. The method according to claim 7, further comprising administering a second therapeutic agent having an antitumor effect.

9. The compound of formula (I), or the pharmaceutically acceptable salt, ester or solvate thereof according to claim 1, wherein the compound is selected from the group consisting of:
   N-(2-((4-nitrophenyl)methoxy)phenyl)-6,7-(benzo-9-crown-3)-4-quinazolinamine (1), N-(3-((4-nitrophenyl)methoxy)phenyl)-6,7-(benzo-9-crown-3)-4-quinazolinamine,
   N-(4-((4-nitrophenyl)methoxy)phenyl)-6,7-(benzo-9-crown-3)-4-quinazolinamine,
   N-(2-((p-fluorophenyl)methoxy)phenyl)-6,7-(benzo-9-crown-3)-4-quinazolinamine,
   N-(3-((p-fluorophenyl)methoxy)phenyl)-6,7-(benzo-9-crown-3)-4-quinazolinamine,
   N-(4-((p-fluorophenyl)methoxy)phenyl)-6,7-(benzo-9-crown-3)-4-quinazolinamine,
   N-(2-((4-trifluoromethylphenyl)methoxy)phenyl)-6,7-(benzo-9-crown-3)-4-quinazolinamine,
   N-(3-((4-trifluoromethylphenyl)methoxy)phenyl)-6,7-(benzo-9-crown-3)-4-quinazolinamine, N-(4-((4-trifluoromethylphenyl)methoxy)phenyl)-6,7-(benzo-9-crown-3)-4-quinazolinamine,
N-(3-((4-cyanophenyl)methoxy)phenyl)-6,7-(benzo-12-crown-4)-4-quinazolinamine,
N-(4-((4-cyanophenyl)methoxy)phenyl)-6,7-(benzo-12-crown-4)-4-quinazolinamine,
N-(2-((4-pyridyl)methoxy)phenyl)-6,7-(benzo-9-crown-3)-4-quinazolinamine,
N-(2-((3-chloro,4-fluorophenyl)methoxy)phenyl)-6,7-(benzo-9-crown-3)-4-quinazolinamine,
N-(3-((3-chloro,4-fluorophenyl)methoxy)phenyl)-6,7-(benzo-9-crown-3)-4-quinazolinamine,
N-(4-((3-chloro,4-fluorophenyl)methoxy)phenyl)-6,7-(benzo-9-crown-3)-4-quinazolinamine,
N-(3-((p-fluorophenyl)methoxy)phenyl)-6,7-(benzo-12-crown-4)-4-quinazolinamine,
N-(4-((p-fluorophenyl)methoxy)phenyl)-6,7-(benzo-12-crown-4)-4-quinazolinamine,
N-(2-((4-nitrophenyl)methoxy)phenyl)-6,7-(benzo-12-crown-4)-4-quinazolinamine,
N-(3-((4-nitrophenyl)methoxy)phenyl)-6,7-(benzo-12-crown-4)-4-quinazolinamine,
N-(4-((4-nitrophenyl)methoxy)phenyl)-6,7-(benzo-12-crown-4)-4-quinazolinamine,
N-(3-((phenyl)methoxy)phenyl)-6,7-(benzo-12-crown-4)-4-quinazolinamine,
N-(2-((4-trifluoromethylphenyl)methoxy)phenyl)-6,7-(benzo-12-crown-4)-4-quinazolinamine,
N-(3-((4-trifluoromethylphenyl)methoxy)phenyl)-6,7-(benzo-12-crown-4)-4-quinazolinamine,
N-(4-((4-trifluoromethylphenyl)methoxy)phenyl)-6,7-(benzo-12-crown-4)-4-quinazolinamine,
N-(3-((p-fluorophenyl)methoxy)phenyl)-6,7-(benzo-15-crown-5)-4-quinazolinamine,
N-(4-((p-fluorophenyl)methoxy)phenyl)-6,7-(benzo-15-crown-5)-4-quinazolinamine,
N-(2-((phenyl)methoxy)phenyl)-6,7-(benzo-15-crown-5)-4-quinazolinamine,
N-(3-((phenyl)methoxy)phenyl)-6,7-(benzo-15-crown-5)-4-quinazolinamine,
N-(4-((phenyl)methoxy)phenyl)-6,7-(benzo-15-crown-5)-4-quinazolinamine,
N-(2-((4-nitrophenyl)methoxy)phenyl)-6,7-(benzo-15-crown-5)-4-quinazolinamine,
N-(3-((4-nitrophenyl)methoxy)phenyl)-6,7-(benzo-15-crown-5)-4-quinazolinamine,
N-(4-((4-nitrophenyl)methoxy)phenyl)-6,7-(benzo-15-crown-5)-4-quinazolinamine,
N-(2-((4-trifluoromethylphenyl)methoxy)phenyl)-6,7-(benzo-15-crown-5)-4-quinazolinamine,
N-(3-((4-trifluoromethylphenyl)methoxy)phenyl)-6,7-(benzo-15-crown-5)-4-quinazolinamine,
N-(4-((4-trifluoromethylphenyl)methoxy)phenyl)-6,7-(benzo-15-crown-5)-4-quinazolinamine,
2-(3-Fluoro-benzyloxy)-5-(7,8,10,11-tetrahydro-6,9,12-trioxa-1,3-diaza-cyclonona[b]naphthalen-4-ylamino)-benzonitrile (36), 3-(3-Fluoro-benzyloxy)-5-(7,8,10,11,13,14-hexahydro-6,9,12,15-tetraoxa-1,3-diaza-cyclododeca[b]naphthalen-4-ylamino)-benzonitrile,
4-(3-Fluoro-benzyloxy)-5-(2,5,8,11,14-pentaoxa-18,20-diaza-tricyclo[13.8.0.0$^{17,22}$]tricosa-16,18,20,22-tetraen-21-ylamino)-benzonitrile.

10. The compound of formula (I), or the pharmaceutically acceptable salt, ester or solvate thereof according to claim 3, wherein the salt formed with an inorganic acid or inorganic base is a hydrochloride salt, a sulfate salt or a phosphate salt.

11. The compound of formula (I), or the pharmaceutically acceptable salt, ester or solvate thereof according to claim 3, wherein the salt formed with an organic acid or organic base is a citrate salt, a p-toluenesulfonate salt, a stearate salt, a succinate salt, a lactate salt, a maleate salt, a tartrate salt, a palmitate salt, a salicylate salt, a dimethylamine salt, a piperidine salt or a morpholine salt.

12. The compound of formula (I), or the pharmaceutically acceptable salt, ester or solvate thereof according to claim 3, wherein the pharmaceutically acceptable cation is formed by the compound of formula (I) with potassium, sodium, calcium, magnesium, aluminum, lithium, zinc or ammonium ions.

13. The pharmaceutical composition according to claim 4, further comprising a pharmaceutically acceptable carrier or excipient.

14. The pharmaceutical composition according to claim 13, wherein the carrier or excipient is selected from the group consisting of water, gelatin, lactose, starch, magnesium stearate, talc, vegetable oil, gum, alcohol, petrolatum and combinations thereof.

15. The pharmaceutical composition according to claim 4, wherein the pharmaceutical composition further comprises a second therapeutic agent selected from regorafenib and sorafenib.

16. The method according to claim 8, wherein the second therapeutic agent is at least one selected from the group consisting of regorafenib, sorafenib, paclitaxel and docetaxel.

\* \* \* \* \*